US012110548B2

(12) United States Patent
Bava

(10) Patent No.: US 12,110,548 B2
(45) Date of Patent: Oct. 8, 2024

(54) BI-DIRECTIONAL IN SITU ANALYSIS

(71) Applicant: 10x Genomics, Inc., Pleasanton, CA (US)

(72) Inventor: Felice Alessio Bava, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 667 days.

(21) Appl. No.: 17/165,802

(22) Filed: Feb. 2, 2021

(65) Prior Publication Data
US 2021/0238674 A1 Aug. 5, 2021

Related U.S. Application Data

(60) Provisional application No. 62/969,575, filed on Feb. 3, 2020.

(51) Int. Cl.
*C12Q 1/6874* (2018.01)
*C12Q 1/6876* (2018.01)

(52) U.S. Cl.
CPC ......... *C12Q 1/6874* (2013.01); *C12Q 1/6876* (2013.01)

(58) Field of Classification Search
None
See application file for complete search history.

(56) References Cited

U.S. PATENT DOCUMENTS

| 4,683,195 | A  | 7/1987  | Mullis et al.       |
| 4,683,202 | A  | 7/1987  | Mullis              |
| 4,800,159 | A  | 1/1989  | Mullis et al.       |
| 4,965,188 | A  | 10/1990 | Mullis et al.       |
| 5,512,462 | A  | 4/1996  | Cheng               |
| 5,635,352 | A  | 6/1997  | Urdea et al.        |
| 5,695,940 | A  | 12/1997 | Drmanac et al.      |
| 6,054,274 | A  | 4/2000  | Sampson et al.      |
| 6,210,891 | B1 | 4/2001  | Nyren et al.        |
| 6,258,568 | B1 | 7/2001  | Nyren et al.        |
| 6,265,552 | B1 | 7/2001  | Schatz              |
| 6,266,459 | B1 | 7/2001  | Walt et al.         |
| 6,274,320 | B1 | 8/2001  | Rothberg et al.     |
| 6,291,187 | B1 | 9/2001  | Kingsmore et al.    |
| 6,306,597 | B1 | 10/2001 | Macevicz            |
| 6,323,009 | B1 | 11/2001 | Lasken et al.       |
| 6,344,329 | B1 | 2/2002  | Lizardi et al.      |
| 6,355,431 | B1 | 3/2002  | Chee et al.         |
| 6,368,801 | B1 | 4/2002  | Faruqi              |
| 6,391,937 | B1 | 5/2002  | Beuhler et al.      |
| 6,534,266 | B1 | 3/2003  | Singer              |
| 6,620,584 | B1 | 9/2003  | Chee et al.         |
| 6,833,246 | B2 | 1/2004  | Balasubramanian et al. |
| 6,770,441 | B2 | 8/2004  | Dickinson et al.    |
| 6,828,100 | B1 | 12/2004 | Ronaghi             |
| 6,859,570 | B2 | 2/2005  | David et al.        |
| 6,911,345 | B2 | 6/2005  | Stephen et al.      |
| 7,057,026 | B2 | 6/2006  | Barnes et al.       |
| 7,166,431 | B2 | 1/2007  | Chee et al.         |
| 7,255,994 | B2 | 8/2007  | Lao                 |
| 7,264,929 | B2 | 9/2007  | Rothberg et al.     |
| 7,473,767 | B2 | 1/2009  | Dimitrov            |
| 7,534,991 | B2 | 5/2009  | Miller et al.       |
| 7,541,444 | B2 | 6/2009  | Milton et al.       |
| 7,555,155 | B2 | 6/2009  | Levenson et al.     |
| 7,563,576 | B2 | 7/2009  | Chee et al.         |
| 7,655,898 | B2 | 2/2010  | Miller              |
| 7,906,285 | B2 | 3/2011  | Drmanac             |
| 7,910,304 | B2 | 3/2011  | Drmanac             |
| 7,941,279 | B2 | 5/2011  | Hwang et al.        |
| 7,960,119 | B2 | 6/2011  | Chee et al.         |
| 7,989,166 | B2 | 8/2011  | Koch et al.         |
| 8,124,751 | B2 | 2/2012  | Pierce et al.       |

(Continued)

FOREIGN PATENT DOCUMENTS

WO  WO 2000/063437  10/2000
WO  WO 2014/025392   2/2014

(Continued)

OTHER PUBLICATIONS

Archer et al., "Selective and flexible depletion of problematic sequences from RNA-seq libraries at the cDNA stage," BMC Genomics. (2014) 15(1):401.
Baner et al., "Signal amplification of padlock probes by rolling circle replication," Nucleic Acids Res. (1998) 26(22):5073-5078.
Bentley et al. "Accurate whole human genome sequencing using reversible terminator chemistry." nature 456.7218 (2008): 53-59.
Berger et al., "Universal bases for hybridization, replication and chain termination," Nucleic Acid Res. (2000) 28(15): 2911-2914.
Bibikova et al., "Quantitative gene expression profiling in formalin-fixed, paraffin-embedded tissues using universal bead arrays," Am J Pathol. Nov. 2004;165(5):1799-807.

(Continued)

*Primary Examiner* — Angela M. Bertagna
*Assistant Examiner* — Carolyn L Greene
(74) *Attorney, Agent, or Firm* — MORRISON & FOERSTER LLP

(57) ABSTRACT

In some aspects, provided herein are methods for analyzing a nucleic acid comprising first and second regions of interest flanking an adaptor region, comprising hybridizing an anchor to the adaptor region, analyzing the first region of interest from one end of the anchor using probe ligation (e.g., sequencing-by-ligation), and binding a polymerase to the other end of the anchor and optionally incorporating a nucleotide and/or analog thereof into the anchor by the polymerase using the second region of interest or a probe bound thereto as a template. In some embodiments, the second region of interest is used as a template for sequencing-by-synthesis. In some embodiments, spatially resolved detections of analytes are performed at a cellular or subcellular resolution which involve correlating signals associated with analytes with specific spatial locations in a biological sample.

16 Claims, 5 Drawing Sheets
Specification includes a Sequence Listing.

(56) References Cited

U.S. PATENT DOCUMENTS

| | | | |
|---|---|---|---|
| 8,199,999 | B2 | 6/2012 | Hoyt et al. |
| 8,206,917 | B2 | 6/2012 | Chee et al. |
| 8,241,573 | B2 | 8/2012 | Banerjee et al. |
| 8,268,554 | B2 | 9/2012 | Schallmeiner |
| 8,330,087 | B2 | 12/2012 | Domenicali |
| 8,415,102 | B2 | 4/2013 | Geiss et al. |
| 8,431,691 | B2 | 4/2013 | McKernan et al. |
| 8,462,981 | B2 | 6/2013 | Determan et al. |
| 8,481,258 | B2 | 7/2013 | Church et al. |
| 8,519,115 | B2 | 8/2013 | Webster et al. |
| 8,551,710 | B2 | 10/2013 | Bernitz et al. |
| 8,563,246 | B2 | 10/2013 | Chee et al. |
| 8,658,361 | B2 | 2/2014 | Wu et al. |
| 8,771,950 | B2 | 7/2014 | Church et al. |
| 8,986,926 | B2 | 3/2015 | Ferree et al. |
| 9,163,283 | B2 | 10/2015 | Chee et al. |
| 9,201,063 | B2 | 12/2015 | Sood et al. |
| 9,273,349 | B2 | 3/2016 | Nguyen et al. |
| 9,371,563 | B2 | 6/2016 | Geiss et al. |
| 9,371,598 | B2 | 6/2016 | Chee |
| 9,376,717 | B2 | 6/2016 | Gao et al. |
| 9,404,155 | B2 | 8/2016 | Bortner |
| 9,512,422 | B2 | 12/2016 | Barnard et al. |
| 9,541,504 | B2 | 1/2017 | Hoyt |
| 9,551,032 | B2 | 1/2017 | Landegren et al. |
| 9,624,538 | B2 | 4/2017 | Church et al. |
| 9,714,446 | B2 | 7/2017 | Webster et al. |
| 9,714,937 | B2 | 7/2017 | Dunaway |
| 9,727,810 | B2 | 8/2017 | Fodor et al. |
| 9,778,155 | B2 | 10/2017 | Gradinaru et al. |
| 9,783,841 | B2 | 10/2017 | Nolan et al. |
| 9,889,422 | B2 | 2/2018 | Smith et al. |
| 9,909,167 | B2 | 3/2018 | Samusik et al. |
| 10,032,064 | B2 | 7/2018 | Hoyt |
| 10,059,990 | B2 | 8/2018 | Boyden et al. |
| 10,126,242 | B2 | 11/2018 | Miller et al. |
| 10,179,932 | B2 | 1/2019 | Church et al. |
| 10,190,162 | B2 | 1/2019 | Drmanac et al. |
| 10,227,639 | B2 | 3/2019 | Levner et al. |
| 10,246,700 | B2 | 4/2019 | Dunaway et al. |
| 10,266,888 | B2 | 4/2019 | Daugharthy et al. |
| 10,267,808 | B2 | 4/2019 | Cai |
| 10,309,879 | B2 | 6/2019 | Chen et al. |
| 10,317,321 | B2 | 6/2019 | Tillberg et al. |
| 10,364,457 | B2 | 7/2019 | Wassie et al. |
| 10,370,698 | B2 | 8/2019 | Nolan et al. |
| 10,415,080 | B2 | 9/2019 | Dunaway et al. |
| 10,457,980 | B2 | 10/2019 | Cai et al. |
| 10,465,235 | B2 | 11/2019 | Gullberg et al. |
| 10,494,662 | B2 | 12/2019 | Church et al. |
| 10,495,554 | B2 | 12/2019 | Deisseroth et al. |
| 10,501,777 | B2 | 12/2019 | Beechem et al. |
| 10,501,791 | B2 | 12/2019 | Church et al. |
| 10,510,435 | B2 | 12/2019 | Cai et al. |
| 10,526,649 | B2 | 1/2020 | Chen et al. |
| 10,545,075 | B2 | 1/2020 | Deisseroth et al. |
| 10,580,128 | B2 | 3/2020 | Miller |
| 10,640,816 | B2 | 5/2020 | Beechem et al. |
| 10,640,826 | B2 | 5/2020 | Church et al. |
| 10,669,569 | B2 | 6/2020 | Gullberg et al. |
| 10,746,981 | B2 | 8/2020 | Tomer et al. |
| 10,774,372 | B2 | 9/2020 | Chee et al. |
| 10,774,374 | B2 | 9/2020 | Frisén et al. |
| 10,794,802 | B2 | 10/2020 | Gradinaru et al. |
| 10,802,262 | B2 | 10/2020 | Tomer et al. |
| 10,815,519 | B2 | 10/2020 | Husain et al. |
| 10,829,814 | B2 | 11/2020 | Fan et al. |
| 10,844,426 | B2 | 11/2020 | Daugharthy et al. |
| 10,851,410 | B2 | 12/2020 | Drmanac et al. |
| 10,858,698 | B2 | 12/2020 | Church et al. |
| 10,872,679 | B2 | 12/2020 | Cai et al. |
| 10,964,001 | B2 | 3/2021 | Miller |
| 11,459,603 | B2 | 10/2022 | Tyagi et al. |
| 2002/0051986 | A1 | 5/2002 | Baez et al. |
| 2009/0026082 | A1 | 1/2009 | Rothberg et al. |
| 2009/0127589 | A1 | 5/2009 | Rothberg et al. |
| 2010/0055733 | A1 | 3/2010 | Lutolf et al. |
| 2010/0137143 | A1 | 6/2010 | Rothberg et al. |
| 2010/0282617 | A1 | 11/2010 | Rothberg et al. |
| 2011/0223585 | A1 | 9/2011 | Gullberg et al. |
| 2013/0288249 | A1 | 10/2013 | Gullbert |
| 2013/0323729 | A1 | 12/2013 | Landegren et al. |
| 2014/0194311 | A1 | 6/2014 | Gullberg et al. |
| 2016/0024555 | A1 | 1/2016 | Church et al. |
| 2016/0108458 | A1 | 4/2016 | Frei et al. |
| 2016/0305856 | A1 | 10/2016 | Boyden et al. |
| 2016/0376642 | A1 | 12/2016 | Landegren et al. |
| 2017/0009278 | A1 | 1/2017 | Söderberg et al. |
| 2017/0029883 | A1 | 2/2017 | Chanfeng et al. |
| 2017/0081489 | A1 | 3/2017 | Rodriques et al. |
| 2017/0101672 | A1 | 4/2017 | Luo et al. |
| 2017/0219465 | A1 | 8/2017 | Desseroth et al. |
| 2017/0220733 | A1 | 8/2017 | Zhuang et al. |
| 2017/0253918 | A1 | 9/2017 | Kohman |
| 2018/0052081 | A1 | 2/2018 | Kohman |
| 2018/0080876 | A1 | 3/2018 | Rockel et al. |
| 2018/0208967 | A1 | 7/2018 | Larman et al. |
| 2018/0237864 | A1 | 8/2018 | Imler et al. |
| 2018/0251833 | A1 | 9/2018 | Daugharthy et al. |
| 2018/0320226 | A1 | 11/2018 | Church et al. |
| 2019/0017106 | A1 | 1/2019 | Frisen et al. |
| 2019/0032128 | A1 | 1/2019 | Chen et al. |
| 2019/0055594 | A1 | 2/2019 | Samusik et al. |
| 2019/0112599 | A1 | 4/2019 | Church et al. |
| 2019/0119735 | A1 | 4/2019 | Deisseroth et al. |
| 2019/0155835 | A1 | 5/2019 | Daugharthy et al. |
| 2019/0161796 | A1 | 5/2019 | Hauling et al. |
| 2019/0177718 | A1 | 6/2019 | Church et al. |
| 2019/0177777 | A1 | 6/2019 | Chee et al. |
| 2019/0194709 | A1 | 6/2019 | Church et al. |
| 2019/0218608 | A1 | 7/2019 | Daugharthy et al. |
| 2019/0249248 | A1 | 8/2019 | Beechem et al. |
| 2019/0264270 | A1 | 8/2019 | Zhuang et al. |
| 2019/0271028 | A1 | 9/2019 | Khafizov et al. |
| 2019/0276881 | A1 | 9/2019 | Zhuang et al. |
| 2019/0339203 | A1 | 11/2019 | Miller et al. |
| 2020/0010891 | A1 | 1/2020 | Beechem et al. |
| 2020/0071751 | A1 | 3/2020 | Daugharthy et al. |
| 2020/0102609 | A1 | 4/2020 | Glezer et al. |
| 2020/0123597 | A1 | 4/2020 | Daniel |
| 2020/0140920 | A1 | 5/2020 | Pierce et al. |
| 2020/0224243 | A1 | 7/2020 | Desai et al. |
| 2020/0224244 | A1 | 7/2020 | Nilsson et al. |
| 2020/0239946 | A1 | 7/2020 | Dewal |
| 2020/0354774 | A1 | 11/2020 | Church et al. |
| 2020/0354782 | A1 | 11/2020 | Dewal |
| 2020/0362398 | A1 | 11/2020 | Kishi et al. |
| 2020/0393343 | A1 | 12/2020 | Kennedy-Darling et al. |
| 2021/0017587 | A1 | 1/2021 | Cai et al. |
| 2021/0115504 | A1 | 4/2021 | Cai et al. |
| 2021/0238662 | A1 | 8/2021 | Bava |
| 2021/0238674 | A1 | 8/2021 | Bava |
| 2021/0254140 | A1 | 8/2021 | Stahl et al. |
| 2021/0262018 | A1 | 8/2021 | Bava et al. |
| 2021/0277460 | A1 | 9/2021 | Bava |
| 2021/0340621 | A1 | 11/2021 | Daugharthy et al. |
| 2021/0388423 | A1 | 12/2021 | Bava et al. |
| 2021/0388424 | A1 | 12/2021 | Bava |
| 2022/0049302 | A1 | 2/2022 | Daugharthy et al. |
| 2022/0049303 | A1 | 2/2022 | Busby et al. |
| 2022/0083832 | A1 | 3/2022 | Shah |
| 2022/0084628 | A1 | 3/2022 | Shah |
| 2022/0084629 | A1 | 3/2022 | Shah |
| 2022/0136049 | A1 | 5/2022 | Bava et al. |
| 2022/0186300 | A1 | 6/2022 | Bava |
| 2022/0195498 | A1 | 6/2022 | Kuhnemund et al. |
| 2022/0213529 | A1 | 7/2022 | Kuhnemund et al. |
| 2022/0228200 | A1 | 7/2022 | Bava |

FOREIGN PATENT DOCUMENTS

| | | |
|---|---|---|
| WO | WO 2014/163886 | 10/2014 |
| WO | WO 2016/162309 | 10/2016 |
| WO | WO 2017/079406 | 5/2017 |

(56) References Cited

FOREIGN PATENT DOCUMENTS

| | | |
|---|---|---|
| WO | WO 2017/143155 | 8/2017 |
| WO | WO-2017147483 A1 * | 8/2017 ............. C12Q 1/682 |
| WO | WO 2019/199579 | 10/2019 |
| WO | WO 2020/056381 | 3/2020 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/155063 | 8/2021 |
| WO | WO 2021/168326 | 8/2021 |

OTHER PUBLICATIONS

Bolognesi et al., "Multiplex Staining by Sequential Immunostaining and Antibody Removal on Routine Tissue Sections," J. Histochem. Cytochem. (2017); 65(8): 431-444.

Capodieci et al., "Gene expression profiling in single cells within tissue," Nat Methods. (2005) 2(9): 663-5.

Chen et al., "Nanoscale imaging of RNA with expansion microscopy," Nat Methods. (2016) 13:679-684.

Chen et al., "Expansion Microscopy," Science (2015) 347(6221):543-548.

Chen et al. "The history and advances of reversible terminators used in new generations of sequencing technology." Genomics, proteomics & bioinformatics 11.1 (2013): 34-40.

Conze et al., "Single molecule analysis of combinatorial splicing," Nucleic Acids Res. (2010) 38(16): e163.

Dean et al., "Rapid Amplification Of Plasmid And Phage DNA Using Phi29 DNA Polymerase And Multiply-Primed Rolling Circle Amplification," Genome Research (2001) 11:1095-1099.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.

Itkovitz et al., "Validating Transcripts with Probes and Imaging Technology," Nat Methods. (2011) 8(4 Suppl): S12-S19.

Itkovitz et al., "Single-molecule transcript counting of stem-cell markers in the mouse intestine," Nat Cell Biol. (2011) 14(1): 106-14.

Jamur et al., "Permeabilization of cell membranes," Method Mol. Biol. (2010) 588: 63-66 (abstract only).

Ju et al., "Four-color DNA sequencing by synthesis using cleavable fluorescent nucleotide reversible terminators," Proc Natl Acad Sci U S A. (2006) 103(52): 19635-19640.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Li et al. "A photocleavable fluorescent nucleotide for DNA sequencing and analysis." Proceedings of the National Academy of Sciences 100.2 (2003): 414-419.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Metzker. "Sequencing technologies—the next generation." Nature reviews genetics. (2010) 11.1: 31-46.

Mohsen et al., "The Discovery of Rolling Circle Amplification and Rolling Circle Transcription," Acc Chem Res. (2016) 49(11): 2540-2550.

Nallur et al., "Signal amplification by rolling circle amplification on DNA microarrays," Nucleic Acids Res. (2001) 29(23): e118.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Ronaghi et al., "A sequencing method based on real-time pyrophosphate," Science. (1998) 281(5375): 363, 365.

Rouhanifard et al. "ClampFISH detects individual nucleic acid molecules using click chemistry-based amplification," Nat Biotechnol. (2018) 17 pages. doi: 10.1038/nbt.4286.

Schweitzer et al., "Multiplexed protein profiling on microarrays by rolling-circle amplification," Nature Biotech. (2002) 20:359-365.

Schweitzer et al. "Immunoassays with rolling circle DNA amplification: A versatile platform for ultrasensitive antigen detection," Proc. Natl Acad. Sci. USA (2000) 97:10113-119.

Soderberg et al. "Characterizing proteins and their interactions in cells and tissues using the in situ proximity ligation assay." *Methods* 45.3 (2008): 227-232.

Sun et al., "Composite organic-inorganic nanoparticles as Raman labels for tissue analysis," Nano Lett. (2007) 7(2): 351-6.

(56) References Cited

OTHER PUBLICATIONS

Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.

Vandernoot et al., "cDNA normalization by hydroxyapatite chromatography to enrich transcriptome diversity in RNA-seq applications," Biotechniques, (2012) 53(6) 373-80.

Wählby et al., "Sequential immunofluorescence staining and image analysis for detection of large numbers of antigens in individual cell nuclei," Cytometry. (2002) 47(1): 32-41.

Weibrecht et al., "Simultaneous visualization of both signaling cascade activity and end-point gene expression in single cells," PLoS One. (2011) 6(5): e20148.

Wilson et al., "Encoded microcarriers for high-throughput multiplexed detection," Angew Chem Int Ed Engl. (2006) 18;45(37): 6104-17.

Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.

Zhao et al., "Advances of multiplex and high throughput biomolecular detection technologies based on encoding microparticles," Sci China Chem. (2011) 54(8):1185.

\* cited by examiner

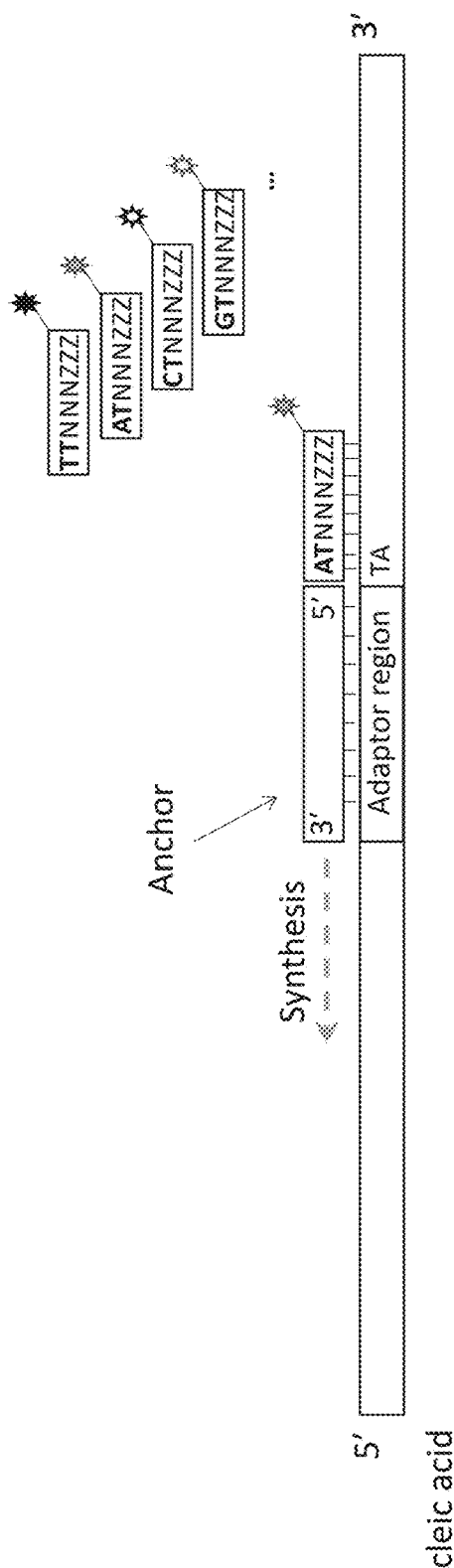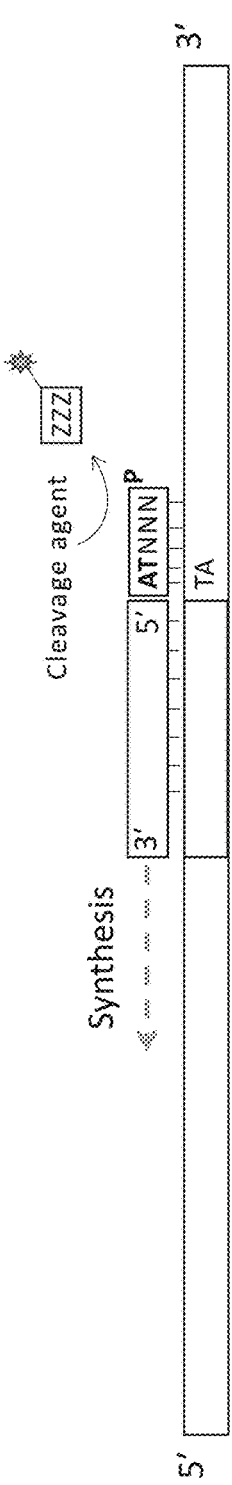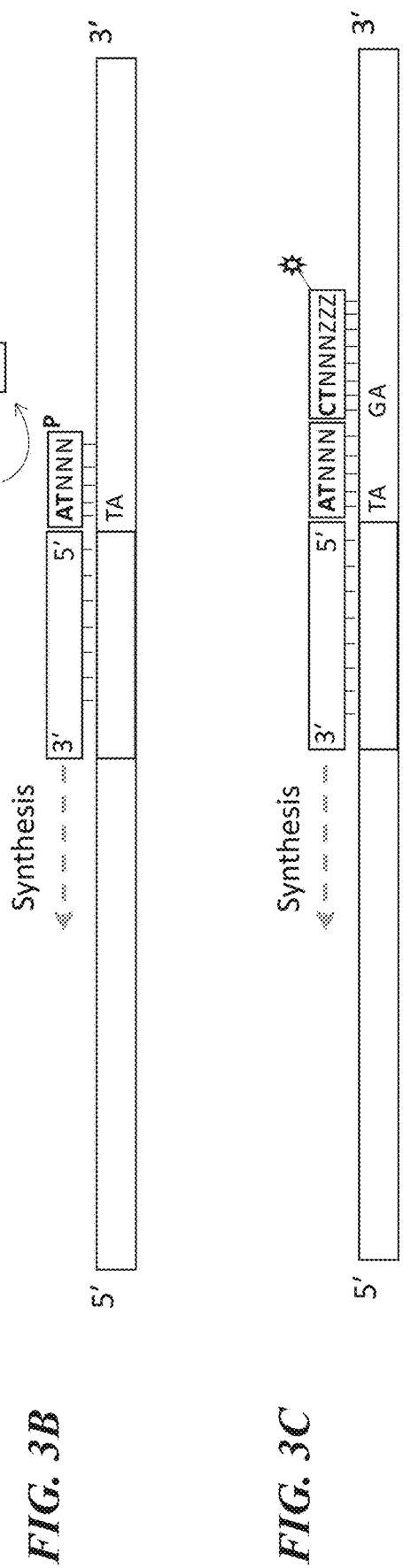
FIG. 3A
FIG. 3B
FIG. 3C

BI-DIRECTIONAL IN SITU ANALYSIS

CROSS-REFERENCE TO RELATED APPLICATION

This application claims priority to U.S. Provisional Application 62/969,575, filed Feb. 3, 2020, entitled "Bi-directional in situ sequencing," the disclosure of which is herein incorporated by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 202412006300SEQLIST.TXT, date recorded: Feb. 2, 2021, size: 823 bytes).

FIELD

The present disclosure generally relates to methods and compositions for analyzing a sample, for example, by performing nucleic acid synthesis (e.g., sequencing by synthesis) on one side of an adaptor region of a nucleic acid in the sample and performing sequencing by ligation on the other side of the adaptor region. The sample may be a cell or tissue sample or an array, and the synthesis and the sequencing by ligation can be performed in situ in the sample.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the positions of the cells and analytes in situ in a parent biological sample (e.g., a tissue sample). Thus, improved methods for in situ analysis are needed. The present disclosure addresses this and other needs.

SUMMARY

In some aspects, provided herein is a method for analyzing a sample, comprising contacting the sample with a plurality of detection probes (e.g., sequencing probes), wherein: the sample comprises a nucleic acid comprising non-overlapping first and second regions of interest flanking an adaptor region that hybridizes to an anchor, each detection probe comprises an interrogatory region and a detectable label, and each detection probe is configured to hybridize to the nucleic acid adjacent to an end of the anchor; ligating a detection probe complementary to the first region of interest to the end of the anchor to generate a ligation product; and detecting a signal associated with the detectable label of the ligation product. In some embodiments, the method further comprises binding a polymerase to the other end of the anchor and optionally incorporating a nucleotide and/or analog thereof into the anchor by the polymerase using the second region of interest or a probe bound thereto (e.g., a primary probe that directly hybridizes to the second region of interest) as a template.

In any of the preceding embodiments, the method can further comprise incorporating the nucleotide and/or analog thereof by the polymerase into the anchor to generate an extended anchor.

In any of the preceding embodiments, the method can further comprise detecting a signal associated with the polymerase and/or the nucleotide or analog thereof binding to the other end of the anchor. In some embodiments, the signal is associated with the nucleotide or analog thereof (e.g., a fluorescently labeled nucleotide or analog thereof) incorporated by the polymerase when extending the anchor.

In any of the preceding embodiments, the method can further comprise contacting the sample with a pool of nucleotides and/or analogs thereof, prior to, during, or after binding of the polymerase to the other end of the anchor. In any of the preceding embodiments, the pool of nucleotides and/or analogs can comprise a natural nucleotide. In any of the preceding embodiments, the pool of nucleotides and/or analogs can comprise a terminator nucleotide or analog thereof. In some embodiments, the terminator nucleotide or analog thereof can be an irreversible terminator, e.g., ddNTP. In any of the preceding embodiments, the terminator nucleotide or analog thereof can be a reversible terminator, e.g., a 3'-unblocked reversible terminator or a 3'-blocked reversible terminator such as a 3'-O-blocked reversible terminator.

In any of the preceding embodiments, the pool of nucleotides and/or analogs thereof can comprise one or more detectably labeled (e.g., fluorescently labeled) nucleotides and/or analogs thereof.

In any of the preceding embodiments, the pool of nucleotides and/or analogs thereof can comprise one or more nucleotides and/or analogs thereof that are not detectably labeled (e.g., fluorescently labeled).

In any of the preceding embodiments, the pool of nucleotides and/or analogs thereof can comprise one or more nucleotides and/or analogs thereof that are detectable by a detectably labeled (e.g., fluorescently labeled) binder, e.g., an antibody or antigen binding fragment thereof, for example, while the one or more nucleotides and/or analogs thereof per se are not detectably labeled. In any of the preceding embodiments, the detectably labeled binder can specifically bind to a reversible terminator nucleotide or analog thereof that is not detectably labeled (e.g., fluorescently labeled).

In any of the preceding embodiments, the method can further comprise incorporating one or more nucleotides or analogs thereof, e.g., a reversible terminator, into the extended anchor. In some embodiments, the incorporated reversible terminator can be modified by removing a reversible terminating group to allow the polymerase to continue extending the extended anchor using the second region of interest or the primary probe bound directly or indirectly to the second region of interest as a template.

In any of the preceding embodiments, the incorporation of the nucleotide and/or analog thereof and signal detection can be repeated to perform sequencing by synthesis, thereby sequencing all or a portion of the second region of interest or primary probe bound thereto.

In any of the preceding embodiments, the anchor can comprise one, two, or more molecules.

In any of the preceding embodiments, the first region of interest, the adaptor region, and the second region of interest can be in the same molecule.

In any of the preceding embodiments, the first region of interest and the second region of interest can be in a first and a second molecule, respectively. In some embodiments, the first and second molecules can hybridize to each other. In some embodiments, the first and second molecules can hybridize to the same molecule (e.g., the anchor) and can be ligated to each other using the anchor as a template.

In any of the preceding embodiments, the first region of interest and/or the second region of interest each can be a single nucleotide of interest.

In any of the preceding embodiments, the first region of interest and/or the second region of interest can each comprise a di-nucleotide or longer sequence of interest.

In any of the preceding embodiments, the detection probes (e.g., sequencing probes) can comprise a sequence of formula $N_xB_yNz$, wherein N is a degenerate base and B is an interrogatory base, x, y, and z are integers independent of each other, wherein x is 0 or greater, y is 1 or greater, and z is 0 or greater, optionally wherein y is 1 or 2 and (x+z) is at least 4.

In any of the preceding embodiments, the interrogatory region of each detection probe can be a single nucleotide, a di-nucleotide, or longer interrogatory nucleotide sequence.

In any of the preceding embodiments, each detection probe can comprise a degenerate sequence and a sequence of universal nucleotides in addition to the interrogatory region.

In any of the preceding embodiments, the detectable label of each detection probe can correspond to a nucleotide or sequence in the interrogatory region.

In any of the preceding embodiments, the plurality of detection probes can comprise detection probes labeled with different detectable labels corresponding to the interrogatory region of each detection probe.

In any of the preceding embodiments, the detectable label of each detection probe can be cleavable.

In any of the preceding embodiments, the detectable label can be cleaved from the ligation product after the detecting step.

In any of the preceding embodiments, all or a portion of the ligation product can be cleaved and/or unhybridized from the nucleic acid after signal detection.

In any of the preceding embodiments, the detection probe can be blocked at the end that is not ligated to the anchor.

In any of the preceding embodiments, the ligation product can be cleaved to regenerate an end for subsequent ligation, optionally wherein the regenerated end can comprise a 5' phosphate group or a 3' hydroxyl group. In some embodiments, the regenerated end comprises a 5' phosphate group for ligation to a detection probe in a subsequent cycle of sequencing by ligation.

In any of the preceding embodiments, the method can comprise repeating the contacting, ligating, and detecting steps in (a) using the same or a different anchor and/or the same or a different plurality of detection probes.

In any of the preceding embodiments, the contacting, ligating, and detecting steps in (a) can be repeated to perform sequencing by ligation, thereby sequencing all or a portion of the first region of interest.

In any of the preceding embodiments, the method can comprise repeating the contacting, ligating, and detecting steps in (a) and/or repeating the binding in (b), e.g., repeating the incorporation of nucleotide and/or analog thereof and signal detection to perform sequencing by synthesis of all or a portion of the second region of interest. In some embodiments, the anchor can remain hybridized to the nucleic acid during one or more cycles of the repeated steps in (a) and/or (b).

In any of the preceding embodiments, the first region of interest can be 3' to the adaptor region, and the detection probe can be ligated to the 5' end of the anchor.

In any of the preceding embodiments, the second region of interest can be 5' to the adaptor region, and the 3' end of the anchor can be extended with the polymerase.

In any of the preceding embodiments, the sample can be contacted with the anchor prior to or during the contacting step in (a).

In any of the preceding embodiments, the contacting, ligating, and/or detecting steps in (a) can be performed prior to the binding step in (b).

In any of the preceding embodiments, the contacting, ligating, and/or detecting steps in (a) can be performed after the binding step in (b).

In any of the preceding embodiments, the nucleic acid can be a viral or cellular DNA or RNA, such as genomic DNA/RNA, mRNA, or cDNA.

In any of the preceding embodiments, the nucleic acid can be endogenous in the sample, and the contacting, ligating, and/or detecting steps in (a) and/or the binding step in (b) can be performed in situ.

In any of the preceding embodiments, the nucleic acid in the sample can be a product (e.g., a hybridization product, a ligation product, an extension product (e.g., by a DNA or RNA polymerase), a replication product, a transcription/reverse transcription product, and/or an amplification product such as a rolling circle amplification (RCA) product) of an endogenous molecule in the sample.

In any of the preceding embodiments, the nucleic acid in the sample can be comprised in a labelling agent that directly or indirectly binds to an analyte in the sample, or can be comprised in a product (e.g., a hybridization product, a ligation product, an extension product (e.g., by a DNA or RNA polymerase), a replication product, a transcription/reverse transcription product, and/or an amplification product such as a rolling circle amplification (RCA) product) of the labelling agent. In some embodiments, the labelling agent can comprise a reporter oligonucleotide, optionally wherein the reporter oligonucleotide comprises one or more barcode sequences and the product of the labelling agent comprises one or a plurality of copies of the one or more barcode sequences.

In any of the preceding embodiments, the nucleic acid in the sample can be a rolling circle amplification (RCA) product of a circular or circularizable (e.g., padlock) probe or probe set that hybridizes to a DNA (e.g., a cDNA of an mRNA) or RNA (e.g., an mRNA) molecule in the sample. In some embodiments, the RCA products of a plurality of different RNA and/or DNA molecules can be analyzed, a barcode sequence in a particular circular or circularizable (e.g., padlock) probe or probe set can uniquely correspond to a particular RNA or DNA molecule, and optionally the particular circular or circularizable (e.g., padlock) probe or probe set can further comprise an anchor sequence that is common among circular or padlock probes for a subset of the plurality of different RNA and/or DNA molecules.

In any of the preceding embodiments, the labelling agent can comprise a binding moiety that directly or indirectly binds to a non-nucleic acid analyte in the sample, e.g., an analyte comprising a peptide, a protein, a carbohydrate, and/or lipid, and the reporter oligonucleotide in the labelling agent can identify the binding moiety and/or the non-nucleic acid analyte. In some embodiments, the binding moiety of the labelling agent can comprise an antibody or antigen binding fragment thereof that directly or indirectly binds to a protein analyte, and the nucleic acid molecule in the sample can be a rolling circle amplification (RCA) product of a circular or circularizable (e.g., padlock) probe or probe set that hybridizes to a reporter oligonucleotide of the labelling agent.

In any of the preceding embodiments, the nucleic acid can be generated in situ, e.g., in a cell or tissue sample or in an array, and the contacting, ligating, and/or detecting steps in (a) and/or the binding step in (b) can be performed in situ, e.g., in a cell or tissue sample or in an array.

In any of the preceding embodiments, the nucleic acid can be immobilized in the sample. In any of the preceding embodiments, the nucleic acid can be crosslinked to one or more molecules (e.g., a cellular molecule or an extracellular molecule) in the sample, a matrix such as a hydrogel, and/or one or more functional groups on a substrate.

In any of the preceding embodiments, the method can comprise imaging the sample to detect the signals, e.g., using fluorescent microscopy. In any of the preceding embodiments, the first and/or second regions of interest can be analyzed in situ in the sample, e.g., using fluorescent microscopy.

In any of the preceding embodiments, the first and/or second regions of interest can comprise one or more barcode sequences, optionally wherein a barcode sequence corresponds to an analyte or a portion (e.g., a biological sequence such as nucleic acid sequence or amino acid sequence) thereof or a labelling agent for the analyte or portion thereof.

In any of the preceding embodiments, the sample can be a processed or cleared biological sample. In any of the preceding embodiments, the sample can be a tissue sample. In some embodiments, the tissue sample can be a tissue slice between about 1 μm and about 50 μm in thickness, optionally wherein the tissue slice is between about 5 μm and about 35 μm in thickness. In some embodiments, the tissue sample can be embedded in a hydrogel.

In any of the preceding embodiments, the sample can comprise an array, such as a random array or an ordered array, of analytes and/or products thereof captured or deposited on a substrate. In some embodiments, the array can be a bead array and the analytes can comprise nucleic acid molecules on the beads. In some embodiments, nucleic acid molecules on a particular bead can comprise one or more barcode sequences corresponding to the location of the bead in the array. In some embodiments, the array can comprise DNA nanoballs on the substrate. In any of the preceding embodiments, the analytes can comprise biomolecules and/or products thereof from a tissue sample.

In some aspects, provided herein is a method for analyzing a sample, comprising: (a) contacting the sample with a plurality of detection probes (e.g., sequencing probes), wherein: the sample comprises a nucleic acid comprising non-overlapping first and second regions of interest flanking an adaptor region that hybridizes to a first anchor, and each detection probe comprises an interrogatory region and a detectable label and is configured to hybridize to the nucleic acid adjacent to the 5' end of the first anchor; ligating a detection probe complementary to the first region of interest to the 5' end of the first anchor to generate a ligation product; and detecting a signal associated with the detectable label of the ligation product, optionally wherein the contacting, ligating, and detecting steps are repeated to determine a sequence of the first region of interest; and (b) contacting the sample with a pool of nucleotides and/or analogs thereof, thereby incorporating a nucleotide or analog thereof by a polymerase into the 3' end of a second anchor hybridized to the adaptor region, wherein the second anchor is extended in the 5' to 3' direction using the second region of interest as a template to generate an extension product; and detecting a signal associated with the incorporated nucleotide or analog thereof in the extension product, optionally wherein the contacting and detecting steps are repeated to determine a sequence of the second region of interest.

In some embodiments, the ligation product can be cleaved after the signal detection in (a), thereby removing the detectable label and optionally a portion of the detection probe ligated to the first anchor prior to a subsequent cycle of the contacting, ligating, and detecting steps in (a).

In any of the preceding embodiments, the ligation product or a portion thereof can be unhybridized from the nucleic acid after the signal detection in (a), thereby removing the ligation product or portion thereof and the detectable label thereon prior to a subsequent cycle of the contacting, ligating, and detecting steps in (a).

In any of the preceding embodiments, the second anchor can comprise the ligation product, a portion thereof, or a further ligation product thereof.

In any of the preceding embodiments, the second anchor can be the ligation product, the portion thereof, or the further ligation product thereof which remains hybridized to the nucleic acid from (a) to (b).

In any of the preceding embodiments, the ligation product, a portion thereof, or a further ligation product thereof can be unhybridized from the nucleic acid prior to (b), and the method can further comprise hybridizing the second anchor to the adaptor region.

In any of the preceding embodiments, the first and second anchors can comprise the same sequence or different sequences.

In any of the preceding embodiments, the method can further comprise: (c) contacting the sample with a plurality of detection probes which may be the same as or different from the plurality of detection probes in (a), wherein: a third anchor is hybridized to the adaptor region and/or a portion of the first region of interest, and each detection probe comprises an interrogatory region and a detectable label and is configured to hybridize to the nucleic acid adjacent to the 5' end of the third anchor; ligating a detection probe complementary to the first region of interest to the 5' end of the third anchor to generate a ligation product; and detecting a signal associated with the detectable label of the ligation product, optionally wherein the contacting, ligating, and detecting steps are repeated to determine a sequence of the first region of interest.

In any of the preceding embodiments, the third anchor can comprise the extension product, a portion thereof, or a further extension product thereof. In some embodiments, the third anchor can be the extension product, the portion thereof, or the further extension product thereof which remains hybridized to the nucleic acid from (b) to (c).

In any of the preceding embodiments, the extension product, the portion thereof, or the further extension product thereof can be unhybridized from the nucleic acid prior to (c), and the method can further comprise hybridizing the third anchor to the adaptor region and/or a portion of the first region of interest.

In any of the preceding embodiments, the first, second, and/or third anchors can comprise the same sequence or different sequences.

In some aspects, provided herein is a method for analyzing a sample, comprising: (a) contacting the sample with a pool of nucleotides and/or analogs thereof, thereby incorporating a nucleotide or analog thereof by a polymerase into the 3' end of a first anchor hybridized to an adaptor region of a nucleic acid in the sample, wherein the nucleic acid comprises non-overlapping first and second regions of interest flanking the adaptor region, wherein the anchor is extended in the 5' to 3' direction using the second region of interest as a template to generate an extension product; and detecting a signal associated with the incorporated nucleotide or analog thereof in the extension product, optionally wherein the contacting and detecting steps are repeated to determine a sequence of the second region of interest; and (b) contacting the sample with a plurality of detection probes, wherein each detection probe comprises an interrogatory region and a detectable label and is configured to hybridize to the nucleic acid adjacent to the 5' end of a second anchor hybridized to the adaptor region; ligating a detection probe complementary to the first region of interest to the 5' end of the second anchor to generate a ligation product; and detecting a signal associated with the detectable label of the ligation product, optionally wherein the contacting, ligating, and detecting steps are repeated to determine a sequence of the first region of interest.

In some embodiments, the second anchor can comprise the extension product, a portion thereof (e.g., the first anchor), or a further extension product thereof which remains hybridized to the nucleic acid from (a) to (b). In other embodiments, the extension product, a portion thereof, or a further extension product thereof can be unhybridized from the nucleic acid prior to (b), and the method can further comprises hybridizing the second anchor to the adaptor region.

In any of the preceding embodiments, the first and second anchors can comprise the same sequence or different sequences.

In any of the preceding embodiments, the method can further comprise: (c) contacting the sample with a pool of nucleotides and/or analogs thereof which may be the same as or different from the pool of nucleotides and/or analogs thereof in (a), thereby incorporating a nucleotide or analog thereof by a polymerase into the 3' end of a third anchor hybridized to the adaptor region and/or a portion of the second region of interest, wherein the third anchor is extended in the 5' to 3' direction using the second region of interest as a template to generate an extension product; and detecting a signal associated with the incorporated nucleotide or analog thereof in the extension product, optionally wherein the contacting and detecting steps are repeated to determine a sequence of the second region of interest.

In some embodiments, the ligation product can be cleaved after the signal detection in (b), thereby removing the detectable label and optionally a portion of the detection probe ligated to the first anchor prior to a subsequent cycle of the contacting, ligating, and detecting steps in (b).

In any of the preceding embodiments, the ligation product or a portion thereof can be unhybridized from the nucleic acid after the signal detection in (b), thereby removing the ligation product or portion thereof and the detectable label thereon prior to a subsequent cycle of the contacting, ligating, and detecting steps in (b).

In any of the preceding embodiments, the third anchor can comprise the ligation product, a portion thereof, or a further ligation product thereof.

In any of the preceding embodiments, the third anchor can be the ligation product, the portion thereof, or the further ligation product thereof which remains hybridized to the nucleic acid from (b) to (c).

In any of the preceding embodiments, the ligation product, a portion thereof, or a further ligation product thereof can be unhybridized from the nucleic acid prior to (c), and the method can further comprise hybridizing the third anchor to the adaptor region and/or a portion of the second region of interest.

In any of the preceding embodiments, the first, second, and/or third anchors can comprise the same sequence or different sequences.

In some aspects, provided herein is a method for decoding an array, comprising: (a) contacting the array with a plurality of detection probes, wherein: the array comprises a plurality of features each comprising multiple nucleic acid molecules on a substrate, wherein a nucleic acid molecule in a feature comprises non-overlapping first and second regions of interest flanking an adaptor region that hybridizes to an anchor, the first and/or second regions of interest comprises one or more barcode sequences, and each detection probe comprises an interrogatory region and a detectable label, and is configured to hybridize to the nucleic acid molecule adjacent to an end of the anchor; ligating a detection probe complementary to the first region of interest to the end of the anchor to generate a ligation product; and detecting a signal associated with the detectable label of the ligation product; (b) contacting the sample with a pool of nucleotides and/or analogs thereof, thereby incorporating a nucleotide or analog thereof by a polymerase into the other end of the anchor, thereby extending the anchor using the second region of interest as a template to generate an extension product; and detecting a signal associated with the incorporated nucleotide or analog thereof in the extension product, wherein the contacting, ligating, and detecting steps in (a) are repeated to determine a sequence of the first region of interest and/or the contacting and detecting steps in (b) are repeated to determine a sequence of the second region of interest, thereby determining the one or more barcode sequences; and (c) associating the one or more barcode sequences in the nucleic acid molecules with the locations of the corresponding features in the array, thereby decoding the array.

In any of the preceding embodiments, the array can be a random array, e.g., a bead array or an array comprising DNA nanoballs.

In some aspects, provided herein is a method of analyzing a sample, comprising: (a) contacting the sample with a plurality of detection probes, wherein the sample comprises a nucleic acid comprising a first region of interest and a second region of interest flanking an adaptor region that hybridizes to an anchor, wherein each detection probe comprises an interrogatory region and a detectable label; ligating a detection probe complementary to the first region of interest to the anchor to generate a ligation product; and detecting a signal from the detectable label of the ligation product; and (b) contacting the sample with a primary probe comprising a sequence complementary to the second region of interest; and extending the anchor with a polymerase using the primary probe as a template.

In some embodiments, the primary probe can comprise a circular probe, a circularizable probe (e.g., a padlock probe), or a probe set that is circularizable.

In any of the preceding embodiments, the extension step in (b) can comprises a rolling circle amplification of the primary probe that is circular or circularized.

In any of the preceding embodiments, the method can comprise hybridizing the primary probe to the second region of interest, wherein the primary probe is adjacent to the 3' end of the anchor.

In any of the preceding embodiments, the primary probe can comprise one or more barcode sequences. In any of the preceding embodiments, the anchor can comprise one or more barcode sequences. In any of the preceding embodiments, the anchor can comprise a region that hybridizes to the primary probe. In any of the preceding embodiments, the ligation product can comprise one or more barcode sequences.

In any of the preceding embodiments, the steps comprising contacting, ligating, and detecting of detection probes can be performed prior to the steps involving the polymerase (e.g., synthesis and/or extension reaction). In any of the preceding embodiments, the steps comprising contacting, ligating, and detecting of detection probes can be performed after the steps involving the polymerase (e.g., synthesis and/or extension reaction).

In any of the preceding embodiments, the steps comprising contacting, ligating, and detecting of detection probes can be repeated multiple cycles to determine a sequence of the first region of interest. In any of the preceding embodiments, the steps involving the polymerase (e.g., synthesis and/or extension reaction) can be repeated multiple cycles. In any of the preceding embodiments, one cycle of the steps comprising contacting, ligating, and detecting of detection probes or the steps involving the polymerase (e.g., synthesis and/or extension reaction) can be prior to or after one or more cycles of the steps comprising contacting, ligating, and detecting of detection probes and/or one or more cycles of the steps involving the polymerase (e.g., synthesis and/or extension reaction).

BRIEF DESCRIPTION OF THE DRAWINGS

FIG. 2B depicts SBL following four cycles of nucleotide incorporation and signal detection for SBS, in alternative embodiments, any number (e.g., one or more) of cycles of SBL can be performed simultaneously with, before, or after any number (e.g., one or more) of cycles of SBS. The anchor, an extended anchor generated in SBS, a ligation product comprising the anchor generated in SBL, or a product after one or more cycles of SBS and/or SBL, may be cleaved and/or stripped, for example, prior to one or more subsequent cycles of SBS and/or SBL. A new anchor may be hybridized to the adaptor region and can be reset (relative to a previous anchor) at a position that is offset by one or more nucleotides (in 5' to 3', 3' to 5', or both directions) prior to performing one or more additional cycles of SBS and/or SBL.

FIGS. 3A-3C show an exemplary variation of SBL. In FIG. 3A, each detection probe (e.g., sequencing probe) comprises an interrogatory nucleotide or sequence (e.g., dinucleotides as shown in the figures) and a sequence of one or more degenerate (N) nucleotides and/or universal nucleotides (Z). As shown in FIG. 3B, in some embodiments, the detection probe comprises a cleavage site, and a cleavage agent can be used to cleave at least the detectable label from the end of the detection probe, thereby regenerating a 5' phosphate. Although the figure depicts the detection probe comprises three degenerate nucleotides and three universal nucleotides, the detection probes can comprise any suitable number of degenerate and/or universal nucleotides (e.g., between 2 and 10, between 2 and 8, or between 3 and 6). Additionally, although the figure depicts cleavage following the third degenerate nucleotide position, the detection probe can be cleaved at any position following the interrogatory sequence. As shown in FIG. 3C, hybridization, ligation, detection, and cleavage of detection probes can be repeated to determine a sequence of the first region of interest. As indicated by the dashed arrows, a synthesis reaction can be performed from the 3' end of the anchor or the ligation product, before or after SBL. The anchor, extended anchor, ligation product comprising the anchor, or extended anchor ligation product can be stripped after one or more cycles of synthesis (e.g., anchor extension or SBS) and/or SBL. In some embodiments, the anchor, extended anchor, ligation product comprising the anchor, or extended anchor ligation product can be cleaved prior to stripping (e.g., cleaved into two or more separate molecules). A new anchor may be hybridized to the adaptor region and can be reset (relative to a previous anchor) at a position that is offset by one or more nucleotides (in 5' to 3', 3' to 5', or both directions) prior to performing one or more additional cycles of synthesis (e.g., anchor extension or SBS) and/or SBL.

As shown in FIG. 5A, the padlock probe can be circularized using the second region of interest as a template. Alternatively, the padlock probe can be circularized using the anchor as a template, as shown in FIG. 5B. In some embodiments, extension comprises a rolling circle amplification (RCA) of the primary probe that is circular or circularized, using the anchor as a primer.

DETAILED DESCRIPTION

Figure 1:
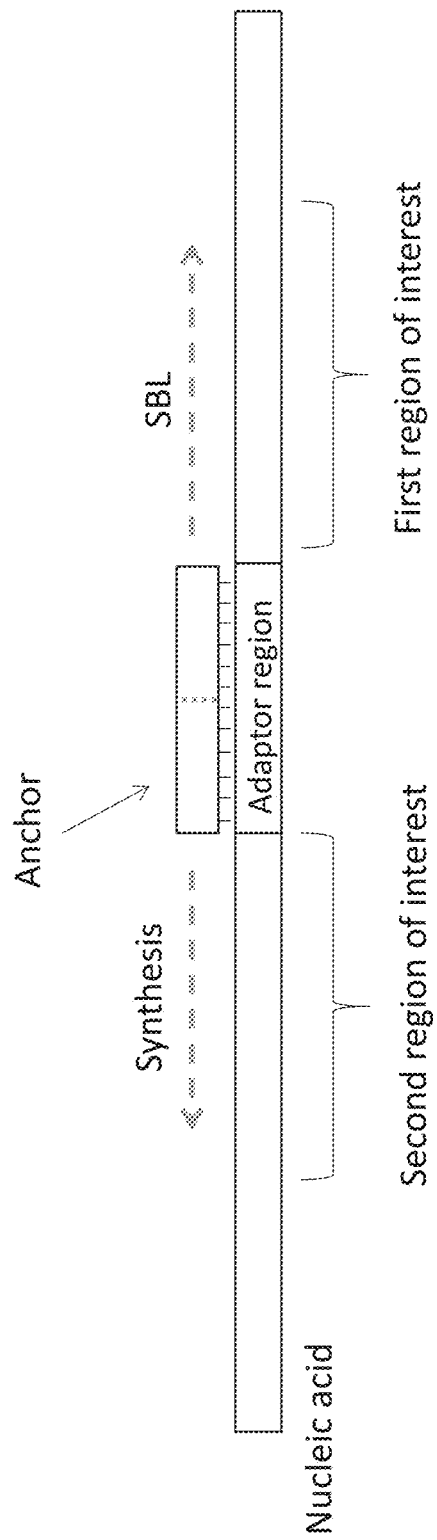
FIG. 1 shows an exemplary method disclosed herein. The first and second regions of interest in the nucleic acid are non-overlapping and flank the adaptor region which hybridizes to the anchor. The anchor can be a single oligonucleotide molecule or can comprise two or more oligonucleotide molecules as indicated by the dashed line. The two or more oligonucleotide molecules can be ligated together using the nucleic acid as a template. Sequencing-by-ligation (SBL) can be used to determine a sequence of the first region of interest (dashed arrow). A synthesis reaction can be performed from the other end of the anchor, thereby extending the anchor.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

In some aspects, provided herein is a method for analyzing a sample, comprising: (a) contacting the sample with a plurality of detection probes, wherein: the sample comprises a nucleic acid comprising non-overlapping first and second regions of interest flanking an adaptor region, the adaptor region hybridizes to a first anchor, and each detection probe comprises an interrogatory region and a detectable label and is configured to hybridize to the nucleic acid adjacent to the 5' end of the first anchor; ligating a detection probe complementary to the first region of interest to the 5' end of the first anchor; and detecting a signal associated with the detectable label of the detection probe ligated to the first anchor to generate a ligation product, optionally wherein the contacting, ligating, and detecting steps are repeated to determine a sequence of the first region of interest; (b) incorporating a nucleotide or analog thereof by a polymerase using the second region of interest as a template into the 3' end of a second anchor hybridized to the adaptor region, thereby extending the second anchor in the 5' to 3' direction to generate an extended second anchor; and detecting a signal associated with the incorporated nucleotide or analog thereof, optionally wherein the incorporating and detecting steps are repeated to determine a sequence of the second region of interest.

In some embodiments, step (b) is a sequencing-by-synthesis reaction. Thus, in one aspect, the present disclosure provides methods to determine the identity of a nucleotide residue in an extension product (e.g., an extension product of the anchor or the ligation product of the anchor and a detection probe).

In some aspects, provided herein are anchor oligonucleotides for use in the methods described herein. In some embodiments, the anchor comprises one, two, or more molecules. In some embodiments, the anchor is between or between about 5 and 50 nucleotides in length, between or between about 5 and 40 nucleotides in length, between or between about 5 and 30 nucleotides in length, between or between about 5 and 20 nucleotides in length, between or between about 10 and 25 nucleotides in length, or between or between about 20 and 35 nucleotides in length.

In some aspects, methods provided herein can be used to analyze a first region of interest and a second region of interest. In some embodiments, the first region of interest, the adaptor region, and the second region of interest are in the same molecule. In some embodiments, the first region of interest and the second region of interest are in a first and a second molecule, respectively. In some embodiments, the first and second molecules hybridize to each other. In some embodiments, the first and second molecules are ligated to each other using the anchor as a template. In some embodiments, the first region of interest and/or the second region of interest each is a single nucleotide of interest. In some embodiments, the first region of interest and/or the second region of interest each comprises a di-nucleotide or longer sequence of interest. In some embodiments, the first region of interest and second region of interest are on the same strand of the nucleic acid. In some embodiments, the first region and second region of interest are not adjacent (i.e., are separated by one or more nucleotides of the adaptor region). In some embodiments, the first region of interest and the second region of interest are separated by between or between about 5 and 40 nucleotides, between or between about 5 and 20 nucleotides, between or between about 10 and 20 nucleotides, or between or between about 15 and 35 nucleotides.

In some aspects, provided herein are detection probes for determining a sequence of the first region of interest in a sequencing-by-ligation reaction. In some embodiments, the detection probes comprise a sequence of formula $N_xB_yN_z$, wherein N is a degenerate base and B is an interrogatory base, x, y, and z are integers independent of each other, wherein x is 0 or greater, y is 1 or greater, and z is 0 or greater, optionally wherein y is 1 or 2 and (x+z) is at least 4. In some embodiments, the interrogatory region of each detection probe is a single nucleotide, a di-nucleotide, or longer interrogatory nucleotide sequence. In some embodiments, each detection probe comprises a degenerate sequence in addition to the interrogatory region. In some embodiments, the detectable label of each detection probe corresponds to a nucleotide or sequence in the interrogatory region. In some embodiments, the plurality of detection probes comprise detection probes labeled with different detectable labels corresponding to the interrogatory region of each detection probe. In some embodiments, the detectable label of each detection probe is cleavable. In some embodiments, the detectable label is cleaved from the detection probe ligated to the anchor after the detecting step. In some embodiments, all or a portion of the detection probe ligated to the anchor is cleaved and/or unhybridized from the nucleic acid after signal detection. In some embodiments, the detection probe is blocked at the end that is not ligated to the anchor. In some embodiments, the detection probe ligated to the anchor is cleaved to regenerate an end for ligation.

In some aspects of the methods provided herein, the method comprises repeating the contacting, ligating, and detecting of detection probes (e.g., steps in (a)) using the same or a different anchor and/or the same or a different plurality of detection probes. In some embodiments, the contacting, ligating, and detecting of detection probes are repeated to perform sequencing by ligation, thereby sequencing all or a portion of the first region of interest. In some embodiments, the method comprises repeating the contacting, ligating, and detecting of detection probes (e.g., steps in (a)) and/or repeating the binding of a polymerase and downstream extension (e.g., step in (b)), e.g., repeating the incorporation of nucleotide and/or analog thereof and signal detection to perform sequencing by synthesis of all or a portion of the second region of interest. In some embodiments, the anchor remains hybridized to the nucleic acid during one or more cycles of the repeated steps of contacting, ligating, and detecting of detection probes and/or binding of the polymerase. In some embodiments, the first region of interest is 3' to the adaptor region, and the detection probe is ligated to the 5' end of the anchor. In some embodiments, the second region of interest is 5' to the adaptor region, and the 3' end of the anchor is extended with the polymerase. In some embodiments, the sample is contacted with the anchor prior to or during the contacting of detection probes with the sample. In some embodiments, one or more iterations of the contacting, ligating, and/or detecting of detection probes is performed prior to one or more iterations of the binding step with the polymerase. In some embodiments, one or more iterations of the contacting, ligating, and/or of detection probes is performed after one or more iterations of the binding step with the polymerase.

In some aspects, a synthesis reaction is performed from the 3' end of the anchor prior to one or more rounds of SBL. In some embodiments, the extension of the anchor using a polymerase stabilizes hybridization of the anchor to the nucleic acid (e.g., the $T_m$ of the extended anchor may be greater than the $T_m$ of the non-extended anchor by about 2° C., about, 3° C., about 4° C., or about 5° C. or greater). In some embodiments, the extended anchor provides additional stability allowing cleavage and removal of detection probes or portions thereof without removal of the hybridized anchor. In other embodiments, one or more rounds of ligation (e.g., SBL) are performed prior to or alternating with one or more rounds of synthesis.

In any of the preceding embodiments, the nucleic acid comprising the regions of interest can be present and/or generated in situ, e.g., in a cell or tissue sample or in an array, and the contacting, ligating, and/or detecting steps (e.g., for SBL) and/or the polymerase-mediated steps (e.g., for SBS) can be performed in situ, e.g., in a cell or tissue sample or in an array. In any of the preceding embodiments, the nucleic acid can be immobilized in the sample. In any of the preceding embodiments, the nucleic acid can be cross-linked to one or more molecules (e.g., a cellular molecule or an extracellular molecule) in the sample, a matrix such as a hydrogel, and/or one or more functional groups on a substrate. In any of the preceding embodiments, the method can comprise imaging the sample to detect the signals, e.g., using fluorescent microscopy. In any of the preceding embodiments, the first and/or second regions of interest can be analyzed in situ in the sample, e.g., using fluorescent microscopy. In any of the preceding embodiments, the first and/or second regions of interest can comprise one or more barcode sequences.

In some aspects, provided herein are methods for analyzing a sample (e.g., decoding a barcode), the method comprising providing a sample comprising a nucleic acid which comprises a adaptor region (e.g., a constant sequence) and a first region of interest (e.g., a first barcode sequence) and a second region of interest (e.g., a second barcode sequence). The sample may be an array comprising a plurality of features on a substrate, wherein a feature of the plurality of features comprises a probe (e.g., a capture probe), wherein the probe comprises a barcode and a constant sequence. In some embodiments, the sample may be a cell or tissue sample, and the nucleic acid may be endogenously present in the sample or generated in situ in the sample. In some aspects, the method further comprises hybridizing an anchor (e.g., a sequencing anchor) to at least a portion of the adaptor region (e.g., the constant sequence). In some aspects, the method further comprises performing sequencing by synthesis on the second region of interest, e.g., the second barcode sequence, thereby decoding the second barcode sequence. In some aspects, the method further comprises performing sequencing by ligation on the first region of interest, e.g., the first barcode sequence, thereby decoding the first barcode sequence. In some aspects, the first and second regions of interest are detected in situ, for example, by SBL and SBS performed in situ in the sample.

In some embodiments, performing sequencing by synthesis comprises (c1) contacting the sample (e.g., an array or a cell or tissue sample) with nucleotide derivatives (e.g., fluorescently labeled nucleotides and/or analogs thereof); (c2) hybridizing a nucleotide derivative to a barcode sequence (e.g., in the second region of interest), wherein the nucleotide derivative comprises a label and is attached to the anchor by a polymerase using the barcode sequence as a template; (c3) obtaining an image of the label with the nucleotide derivative hybridized to the barcode and attached to the anchor; (c4) determining, based on the image, a position of a nucleotide in the barcode sequence. In some embodiments, the method comprises repeating steps (c1) through (c4) until substantially all of the barcode has been decoded. In some embodiments, the probe (e.g., the capture probe) comprises a constant sequence in an interior portion of the barcode, wherein the barcode comprises a first portion flanking one side of the constant sequence and a second portion flanking the other side of the constant sequence. In some embodiments, step (c1) through (c4) can be repeated until substantially all of the second region of interest has been decoded.

In some embodiments, the method further comprises: (d) performing sequencing by ligation to decode a barcode sequence (e.g., in the first region of interest). In some embodiments, performing sequencing by ligation comprises (d1) ligating a first detection probe complementary to the barcode sequence to the free end of the anchor (e.g., the sequencing anchor) that is not the end extended by a polymerase, wherein the first detection probe comprises a label and a nucleic acid sequence; (d2) obtaining an image of the label with the detection probe hybridized to the barcode; (d3) determining, based on the image, one or more nucleotides of the barcode. In some embodiments, the method comprises repeating steps (d1) through (d3) until substantially all of the barcode has been decoded. In some embodiments, the method comprises repeating step (d1) through (d3) until substantially of the second portion of the barcode has been decoded. In some embodiments, the nucleotide derivatives comprise 5' triphosphates of 2'deoxy-adenosine, 2'-deoxyguanosine, 2'-deoxycytidine and 2'-deoxythymidine, wherein each nucleotide derivative comprises a 3' blocking group and an optical label distinguishable from the optical labels of the other nucleotide derivatives. In some embodiments, the optical labels of the nucleotide derivatives are identified using optical detection.

In some embodiments, the hybridizing step (c2) further comprises: (i) providing a composition comprising an enzyme; and a plurality of nucleotide derivatives; and (ii) coupling a nucleotide derivative to the free 3' end of the anchor based on the complementarity of the nucleotide derivative to a nucleotide of the barcode. In some embodiments, the method further comprises (iii) washing the sample (e.g., an array or a cell or tissue sample) to remove any nucleotide derivatives not hybridized to the first barcode. In some embodiments, the enzyme comprises a DNA polymerase or a DNA ligase. In some embodiments, the DNA ligase is a T4 DNA ligase.

In some embodiments, the method further comprises removing the 3' blocking group of the hybridized nucleotide derivative, and adding an OH group at the 3' position. In some embodiments, removing the 3' blocking group and adding an OH group occurs after step (c4). In some embodiments, determining the nucleotide in a position of the barcode comprises identifying the nucleotide derivative in the image based on the label, and identifying the nucleotide in the position of the barcode as a nucleotide complement to the nucleotide derivative coupled to the nucleotide in the position of the barcode. In some embodiments, the method comprises repeating steps (c1) through (c4) with one or more additional nucleotide derivatives, wherein each additional nucleotide derivative comprises a 3' blocking group, a known label, and a known nucleotide, until the sequence of the barcode is all or partially determined. In some embodiments, repeating steps (c1) through (c4) comprises hybridizing the one or more additional nucleotide derivatives to the most recently coupled nucleotide derivative comprising a free 3' end. In some embodiments, the free 3' end comprises an OH group. In some embodiments, ligating the first detection probe complementary to the barcode to the anchor comprises: contacting the barcode with a composition of sequencing probes, wherein each member of the composition of sequencing probes comprises a known, different nucleotide at a 3' sequence position and a known, different label; and coupling a detection probe from the composition of detection ("sequencing") probes to the free 5' end of the anchor, thereby ligating the first detection probe that is complementary to the anchor to the barcode. In some embodiments, determining one or more nucleotides of the barcode comprises identifying the nucleotide at the 3' sequence position of the first detection probe based on the image of the label, and identifying the one or more nucleotides of the barcode as a nucleotide complement to the nucleotide at the 3' sequence position of the first sequencing probe. In some embodiments, the method comprises repeating steps (d1) through (d3) with one or more additional sequencing probes, each additional detection probe comprising a label and a nucleotide sequence, until the sequence of the barcode is all or partially determined.

In some embodiments, a method further comprises (e1) ligating the additional detection probe to the barcode; (e2) obtaining an image of the label with the additional detection probe hybridized to the barcode; and (e3) determining, based on the image, a second one or more nucleotides of the barcode. In some embodiments, ligating the additional detection probe to the barcode comprises: contacting the barcode with a composition of sequencing probes, wherein each member of the composition of sequencing probes each comprises a known, different nucleotide at a 3' sequence position and a known, different label; and coupling a detection probe from the composition of detection probes to the free 5' end of the anchor or to the free 5' end of at least a portion of the first sequencing probe, thereby ligating the additional detection probe to the barcode. In some embodiments, determining the second one or more nucleotides of the barcode comprises identifying the nucleotide at the 3' sequence position of the additional detection probe based on the image of the label associated with the additional sequencing probe, and identifying the second one or more nucleotides of the barcode as a nucleotide complement to the nucleotide at the 3' sequence position of the additional sequencing probe.

In some embodiments, a method further comprises amplifying at least a portion of the capture probe before determining the sequence of the barcode. In some embodiments, amplifying the at least a portion of the capture probe comprises isothermal or non-isothermal amplification. In some embodiments, determining substantially all of the sequence of the barcode comprises sequentially hybridizing each of three or more detection probes to the barcode. In some embodiments, determining substantially all of the sequence of the barcode comprises sequentially hybridizing each of ten of more detection probes of the barcode. In some embodiments, the barcode comprises n nucleotides, and determining all or a portion of the sequence of the barcode comprises sequentially hybridizing n different detection probes to the barcode. In some embodiments, the barcode comprises n nucleotides, and determining all or a portion of the sequence of the barcode comprises sequentially hybridizing fewer than n different detection probes to the barcode. In some embodiments, a method further comprises removing all of the first detection probe from the barcode, and coupling the additional detection probe to the free 5' end of the anchor (e.g., the sequencing anchor).

In some embodiments, the method further comprises removing a portion of the first detection probe from the barcode, and coupling the additional detection probe to a free 5' end of the first detection probe that remains hybridized to the barcode. In some embodiments, the first detection probe comprises a first nucleotide sequence, and wherein a known nucleotide is located at a first 3' sequence position relative to the 3' end of the first nucleotide sequence. In some embodiments, each of the nucleotides in the first nucleotide sequence, other than the known nucleotide, is a universal base. In some embodiments, the length of the first nucleotide sequence is the same as the length of the second portion of the barcode. In some embodiments, the additional detection probe comprises a second nucleotide sequence, and wherein a known nucleotide is located at a first 3' sequence position relative to the 3' end of the second nucleotide sequence. In some embodiments, each of the nucleotides in the second nucleotide sequence, other than the known nucleotide, is a universal base. In some embodiments, the length of the second nucleotide sequence is the same as the length of the second portion of the barcode.

In some embodiments, the additional detection probe comprises a second nucleotide sequence, and wherein a known nucleotide is located at a second 3' sequence position relative to the 3' end of the second nucleotide sequence. In some embodiments, each of the nucleotides in the second nucleotide sequence, other than the known nucleotide, is a universal base. In some embodiments, a length of the second nucleotide sequence is the same as the length of the second portion of the barcode. In some embodiments, the first detection probe comprises a label coupled to the 5' end of the first nucleotide sequence, wherein the additional detection probe comprises a label coupled to the 5' end of the second nucleotide sequence. In some embodiments, the first detection probe comprises a first nucleotide sequence, and wherein known nucleotides are located at two 3' sequence positions of the first nucleotide sequence. In some embodiments, the two 3' sequence positions are first and second sequence positions relative to the 3' end of the first nucleotide sequence. In some embodiments, each of the nucleotides in the first nucleotide sequence, other than the known nucleotides, is a universal base. In some embodiments, a length of the first nucleotide sequence is the same as a length of the second portion of the barcode. In some embodiments, the additional detection probe comprises a second nucleotide sequence, and wherein known nucleotides are located at two 3' sequence positions of the second nucleotide sequence. In some embodiments, the two 3' sequence positions are first and second sequence positions relative to the 3' end of the second nucleotide sequence. In some embodiments, the two 3' sequence positions are third and fourth positions relative to the 3' end of the second nucleotide sequence. In some embodiments, each of the nucleotides in the second nucleotide sequence, other than the known nucleotides, is a universal base.

In some embodiments, a length of the second nucleotide sequence is the same as the length of the second portion of the barcode. In some embodiments, removing the first detection probe from the barcode comprises cleaving the first detection probe to generate a free 5' end capable of serving as substrate in a ligation reaction. In some embodiments, the method comprises removing at least the label from the first sequencing probe. In some embodiments, a method further comprising cleaving the first detection probe with a nuclease. In some embodiments, the first detection probe comprises a nuclease recognition site. In some embodiments, a method further comprises removing the anchor (e.g., the sequencing anchor) after determining substantially all of the second portion of the barcode. In some embodiments, a method further comprises removing the anchor after determining substantially all of the barcode.

In some embodiments, the label comprises at least one of an optical label, a radioactive label, a fluorescent label, an enzymatic label, a chemiluminescent label, a bioluminescent label, or a dye. In some embodiments, the probe further comprises a capture domain. In some embodiments, the capture probe comprises, from 5' to 3', the barcode, the constant sequence, and the capture domain. In some embodiments, the capture probe comprises, from 5' to 3', the constant sequence, the barcode, and the capture domain. In some embodiments, the capture probe comprises, from 5' to 3', the barcode, the constant sequence and the capture domain. In some embodiments, the barcode comprises, from 5' to 3', a second region of interest and a second portion of the barcode. In some embodiments, the barcode comprises, from 5' to 3', a second region of interest, a constant sequence, and a second portion of the barcode. In some embodiments, the second region of interest and the second portion of the barcode are different. In some embodiments, one or more features of the plurality of features comprises a plurality of capture probes. In some embodiments, a method further comprises determining the barcode sequence for two or more locations in the sample (e.g., locations in a cell or tissue sample indicated by detected signal "spots" or features in an array). In some embodiments, the barcode associated with a feature is unique relative to barcodes associated with other features in the array. In some embodiments, the first barcode and the second barcode are unique relative to first and second barcodes associated with other features in the array.

Provided herein are methods for decoding a barcode, the method comprising: (a) providing an array comprising a plurality of features on a substrate, wherein a feature of the plurality of features comprises a probe, wherein the probe comprises a barcode and an adaptor region (e.g., a constant sequence), and optionally a capture domain; (b) determining the sequence of the barcode and associating the feature with a location in the array; (c) optionally capturing an analyte of a biological sample with the capture domain; and (d) optionally determining the location of the captured analyte in the biological sample based on the location of the feature in the array, wherein determining the sequence of the barcode and associating the feature with the location in the array comprises performing sequencing by synthesis on the barcode, thereby decoding the barcode. In some embodiments, the method comprises performing sequencing by synthesis on one side of the adaptor region (e.g., the constant sequence) and performing sequencing by ligation on the other side of the adaptor region (e.g., the constant sequence).

In some embodiments, performing sequencing by synthesis comprises (c1) contacting an array with nucleotide derivatives; (c2) hybridizing a nucleotide derivative to the barcode, wherein the nucleotide derivative comprises a label and a nucleic acid; (c3) obtaining an image of the label with the nucleotide derivative hybridized to the barcode; (c4) determining, based on the image, the position of a nucleotide in the barcode sequence. In some embodiments, the capturing step (c) comprises contacting the array with the biological sample and allowing the analyte to interact with the capture probe. In some embodiments, the barcode comprises a constant sequence in an interior portion of the barcode, wherein the barcode comprises a first portion flanking one side of the constant sequence and a second portion flanking the other side of the constant sequence. In some embodiments, repeating steps (c1) through (c4) until substantially all of the second region of interest has been decoded. In some embodiments, performing sequencing by synthesis occurs prior to removing the biological sample from the array. In some embodiments, a method further comprises (d) performing sequencing by ligation to decode the barcode.

In some embodiments, performing sequencing by ligation comprises (d1) ligating a first detection probe to the barcode, wherein the first detection probe comprises a label and a nucleotide sequence; (d2) obtaining an image of the label with the detection probe hybridized to the barcode; (d3) determining, based on the image, one or more nucleotides of the barcode sequence. In some embodiments, repeating steps (d1) through (d3) until substantially all of the second portion of the barcode has been decoded. In some embodiments, the method further comprises removing the biological sample from the array. In some embodiments, performing sequencing by ligation occurs prior to removing the biological sample from the array. In some embodiments, performing sequencing by ligation occurs after removing the biological sample from the array.

Provided herein are methods for decoding a barcode, the method comprising: (a) providing an array comprising a plurality of features on a substrate, wherein a feature of the plurality of features comprises a capture probe, wherein the capture probe comprises a barcode, a constant sequence, and a capture domain; (b) determining the sequence of the barcode and associating the feature with a location in the array; (c) capturing an analyte of a biological sample with the capture domain; and (d) determining the location of the captured analyte in the biological sample based on the location of the feature in the array, wherein determining the sequence of the barcode and associating the feature with the location in the array comprises performing sequencing by ligation on the barcode, thereby decoding the barcode. In some embodiments, the method comprises performing sequencing by synthesis on one side of the adaptor region (e.g., the constant sequence) and performing sequencing by ligation on the other side of the adaptor region (e.g., the constant sequence).

In some embodiments, performing sequencing by ligation comprises (d1) ligating a first detection probe to the barcode, wherein the first detection probe comprises a label and a nucleotide sequence; (d2) obtaining an image of the label with the detection probe hybridized to the barcode; (d3) determining, based on the image, one or more nucleotides of the barcode sequence. In some embodiments, the capturing step (c) comprises contacting the array with the biological sample and allowing the analyte to interact with the capture probe. In some embodiments, the barcode comprises a constant sequence in an interior portion of the barcode and the barcode comprises a first portion flanking one side of the constant sequence and a second portion flanking the other side of the constant sequence. In some embodiments, repeating steps (d1) through (d3) until substantially all of the second portion of the barcode has been decoded. In some embodiments, the method further comprises removing the biological sample from the array. In some embodiments, performing sequencing by ligation occurs prior to removing the biological sample from the array.

In some embodiments, the method further comprises performing sequencing by synthesis to decode the barcode. In some embodiments, performing sequencing by synthesis comprises (c1) contacting an array with nucleotide derivatives; (c2) hybridizing a nucleotide derivative to the barcode, wherein the nucleotide derivative comprises a label and a nucleotide; (c3) obtaining an image of the label with the nucleotide derivative hybridized to the barcode; (c4) determining, based on the image, the position of a nucleotide in the barcode sequence. In some embodiments, repeating steps (c1) through (c4) until substantially all of the second region of interest has been decoded.

In some embodiments, performing sequencing by synthesis occurs prior to removing the biological sample from the array. In some embodiments, performing sequencing by synthesis occurs after removing the biological sample from the array. In some embodiments, the capture domain can hybridize to a nucleotide sequence present on or associated with the analyte. In some embodiments, capturing the analyte of the biological sample with the capture domain comprises releasing the capture probe from the array and contacting the biological sample with the released capture probe. In some embodiments, the analyte comprises DNA or RNA. In some embodiments, the analyte comprises a protein.

II. Samples, Analytes, and Target Sequences

A method disclosed herein may be used to process and/or analyze any analyte(s) of interest, for example, for detecting the analyte(s) in situ in a sample of interest. A target nucleic acid sequence for an anchor disclosed herein may be or be comprised in an analyte (e.g., a nucleic acid analyte, such as genomic DNA, mRNA transcript, or cDNA, or a product thereof, e.g., an extension or amplification product, such as an RCA product) and/or may be or be comprised in a labelling agent for one or more analytes (e.g., a nucleic acid analyte or a non-nucleic acid analyte) in a sample or a product of the labelling agent. Exemplary analytes and labelling agents are described below. In some embodiments, the target nucleic acid sequence is in an amplification product formed using isothermal amplification or non-isothermal amplification, optionally rolling circle amplification (RCA). In some embodiments, the target nucleic acid sequence is in a probe or probe set that targets the amplification product. In some embodiments, the target nucleic acid sequence comprises a barcode sequence corresponding to an analyte. In some embodiments, the target nucleic acid sequence comprises two or more regions of interest (e.g., sequences).

In some aspects, the methods disclosed herein may be used to detect the analyte(s) in situ by preserving or retaining the spatial location of the analyte or a derivative of the analyte. For example, the method may substantially retain the relative three-dimensional spatial relationship of the analyte(s) in the biological sample from which the analytes are derived or obtained.

A. Samples

A sample disclosed herein can be or be derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include an array of tissues, cells, and/or molecules. The array may be a random array or an ordered array. The array may be on a solid support, and can include a two-dimensional (2D) surface or a three-dimensional (3D) matrix. In some embodiments, a 2D array comprises analytes (e.g., protein, RNA, and/or DNA) on a 2D surface. In some embodiments, a 2D array comprises amplicons (e.g., rolling circle amplification products) derived from analytes (e.g., protein, RNA, and/or DNA) on a 2D surface. In some embodiments, a 2D surface may comprise a glass, plastic, or metal surface, optionally coated with a polymer, particle, protein, or combination thereof. In some embodiments, a 3D array comprises analytes (e.g., protein, RNA, and/or DNA) in a 3D matrix. In some embodiments, a 3D array comprises amplicons (e.g., rolling circle amplification products) derived from analytes (e.g., protein, RNA, and/or DNA) in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

In some embodiments, the biological sample can be embedded in a hydrogel matrix. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., Science 347(6221):543-548, 2015, the entire contents of which are incorporated herein by reference.

(v) Staining

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine.

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65(8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

(vi) Isometric Expansion

In some embodiments, a biological sample embedded in a hydrogel can be isometrically expanded. Isometric expansion methods that can be used include hydration, a preparative step in expansion microscopy, as described in Chen et al., Science 347(6221):543-548, 2015.

Isometric expansion can be performed by anchoring one or more components of a biological sample to a gel, followed by gel formation, proteolysis, and swelling. Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation method known in the art. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some embodiments, one or more nucleic acid probes can be used to hybridize to a target nucleic acid (e.g., cDNA or RNA molecule, such as an mRNA) and ligated in a templated ligation reaction (e.g., RNA-templated ligation (RTL) or DNA-templated ligation (e.g., on cDNA)) to generate a product for analysis. In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, BMC Genomics, 15 401, (2014), the entire contents of which are incorporated herein by reference). Furthermore, hydroxyapatite chromatography can remove abundant species (e.g., rRNA) (see, e.g., Vandernoot, V.A., cDNA normalization by hydroxyapatite chromatography to enrich transcriptome diversity in RNA-seq applications, Biotechniques, 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprises one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S.

Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adaptor sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed.

a. Hybridization

In some embodiments, a product of an endogenous analyte and/or a labelling agent is a hybridization product comprising the pairing of substantially complementary or complementary nucleic acid sequences within two different molecules, one of which is the endogenous analyte or the labelling agent. The other molecule can be another endogenous molecule or another labelling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various probes and probe sets can be hybridized to an endogenous analyte and/or a labelling agent and each probe may comprise one or more barcode sequences. Exemplary barcoded probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary.

b. Ligation

In some embodiments, a product of an endogenous analyte and/or a labelling agent is a ligation product. In some embodiments, the ligation product is formed between two or more endogenous analytes. In some embodiments, the ligation product is formed between an endogenous analyte and a labelling agent. In some embodiments, the ligation product is formed between two or more labelling agent. In some embodiments, the ligation product is an intramolecular ligation of an endogenous analyte. In some embodiments, the ligation product is an intramolecular ligation of a labelling agent, for example, the circularization of a circularizable probe or probe set upon hybridization to a target sequence. The target sequence can be comprised in a endogenous analyte (e.g., genomic DNA or mRNA) or a product thereof (e.g., cDNA from a cellular mRNA transcript), or in a labelling agent (e.g., the reporter oligonucleotide) or a product thereof.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety. In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety.

In some embodiments, a probe such as a padlock probe may be used to analyze a reporter oligonucleotide, which may generated using proximity ligation or be subjected to proximity ligation. In some examples, the reporter oligonucleotide of a labelling agent that specifically recognizes a protein can be analyzed using in situ hybridization (e.g., sequential hybridization) and/or in situ sequencing (e.g., using padlock probes and rolling circle amplification of ligated padlock probes). Further, the reporter oligonucleotide of the labelling agent and/or a complement thereof and/or a product (e.g., a hybridization product, a ligation product, an extension product (e.g., by a DNA or RNA polymerase), a replication product, a transcription/reverse transcription product, and/or an amplification product) thereof can be recognized by another labelling agent and analyzed.

In some embodiments, an analyte (a nucleic acid analyte or non-nucleic acid analyte) can be specifically bound by two labelling agents (e.g., antibodies) each of which is attached to a reporter oligonucleotide (e.g., DNA) that can participate in ligation, replication, and sequence decoding reactions, e.g., using a probe or probe set (e.g. a padlock probe, a SNAIL probe set, a circular probe, or a padlock probe and a connector). In some embodiments, the probe set may comprise two or more probe oligonucleotides, each comprising a region that is complementary to each other. For example, a proximity ligation reaction can include reporter oligonucleotides attached to pairs of antibodies that can be joined by ligation if the antibodies have been brought in proximity to each other, e.g., by binding the same target protein (complex), and the DNA ligation products that form are then used to template PCR amplification, as described for example in Söderberg et al., Methods. (2008), 45(3): 227-32, the entire contents of which are incorporated herein by reference. In some embodiments, a proximity ligation reaction can include reporter oligonucleotides attached to antibodies that each bind to one member of a binding pair or complex, for example, for analyzing a binding between members of the binding pair or complex. For detection of analytes using oligonucleotides in proximity, see, e.g., U.S. Patent Application Publication No. 2002/0051986, the entire contents of which are incorporated herein by reference. In some embodiments, two analytes in proximity can be specifically bound by two labelling agents (e.g., antibodies) each of which is attached to a reporter oligonucleotide (e.g., DNA) that can participate, when in proximity when bound to their respective targets, in ligation, replication, and/or sequence decoding reactions In some embodiments, one or more reporter oligonucleotides (and optionally one or more other nucleic acid molecules such as a connector) aid in the ligation of the probe. Upon ligation, the probe may form a circularized probe. In some embodiments, one or more suitable probes can be used and ligated, wherein the one or more probes comprise a sequence that is complementary to the one or more reporter oligonucleotides (or portion thereof). The probe may comprise one or more barcode sequences. In some embodiments, the one or more reporter oligonucleotide may serve as a primer for rolling circle amplification (RCA) of the circularized probe. In some embodiments, a nucleic acid other than the one or more reporter oligonucleotide is used as a primer for rolling circle amplification (RCA) of the circularized probe. For example, a nucleic acid capable of hybridizing to the circularized probe at a sequence other than sequence(s) hybridizing to the one or more reporter oligonucleotide can be used as the primer for RCA. In other examples, the primer in a SNAIL probe set is used as the primer for RCA.

In some embodiments, one or more analytes can be specifically bound by two primary antibodies, each of which is in turn recognized by a secondary antibody each attached to a reporter oligonucleotide (e.g., DNA). Each nucleic acid molecule can aid in the ligation of the probe to form a circularized probe. In some instances, the probe can comprise one or more barcode sequences. Further, the reporter oligonucleotide may serve as a primer for rolling circle amplification of the circularized probe. The nucleic acid molecules, circularized probes, and RCA products can be analyzed using any suitable method disclosed herein for in situ analysis.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature (Tm) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

c. Primer Extension and Amplification

In some embodiments, a product here is a primer extension product of an analyte, a labelling agent, a probe or probe set bound to the analyte (e.g., a padlock probe bound to genomic DNA, mRNA, or cDNA), or a probe or probe set bound to the labelling agent (e.g., a padlock probe bound to one or more reporter oligonucleotides from the same or different labelling agents).

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. A primer extension reaction generally refers to any method where two nucleic acid sequences become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 November 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, WO 2014/163886, WO 2017/079406, US 2016/0024555, US 2018/0251833 and WO2014/025392. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. As noted above, many assays are known for the detection of numerous different analytes, which use a RCA-based detection system, e.g., where the signal is provided by generating a RCP from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (i.e. a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some embodiments, a product herein includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for an anchor (e.g., the sequencing anchor) or probe disclosed herein (e.g., a padlock probe) may be a hybridization complex formed of a cellular nucleic acid in a sample and an exogenously added nucleic acid probe. The exogenously added nucleic acid anchor or probe may comprise an overhang that does not hybridize to the cellular nucleic acid but hybridizes to another probe (e.g., a detectably labelled probe such as a circularizable probe or probe set). The exogenously added nucleic acid anchor or probe may be optionally ligated to a cellular nucleic acid molecule or another exogenous nucleic acid molecule. In other examples, a product comprising a target sequence for an anchor (e.g., the sequencing anchor) or probe disclosed herein may be an RCP of a circularizable probe or probe set which hybridizes to a cellular nucleic acid molecule (e.g., genomic DNA or mRNA) or product thereof (e.g., a transcript such as cDNA, a DNA-templated ligation product of two probes, or an RNA-templated ligation product of two probes). In other examples, a product comprising a target sequence for an anchor (e.g., the sequencing anchor) or probe disclosed herein may be a probe hybridizing to an RCP.

C. Target Sequences

A target sequence (e.g., a region of interest and/or an adaptor region) herein may be comprised in any analyte disclose herein, including an endogenous analyte (e.g., a viral or cellular nucleic acid), a labelling agent, or a product of an endogenous analyte and/or a labelling agent. The target sequence for an anchor (e.g., the sequencing anchor) disclosed herein may be flanked by additional target sequences (e.g., regions of interest), which may similarly be comprised in any analyte disclose herein, including an endogenous analyte (e.g., a viral or cellular nucleic acid), a labelling agent, or a product of an endogenous analyte and/or a labelling agent.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding embodiments, barcodes (e.g., primary and/or secondary barcode sequences) can be analyzed (e.g., detected or sequenced) using a method described herein or steps thereof in combination with or in addition to any suitable methods or techniques, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), sequencing by synthesis (SBS), sequencing by ligation (SBL), sequencing by hybridization (SBH), or spatially-resolved transcript amplicon readout mapping (STARmap). In any of the preceding embodiments, the methods provided herein can include analyzing the barcodes by sequential hybridization and detection with a plurality of labelled probes (e.g., detection probes or oligonucleotides).

In some embodiments, in a barcode sequencing method, barcode sequences are detected for identification of other molecules including nucleic acid molecules (DNA or RNA)

longer than the barcode sequences themselves, as opposed to direct sequencing of the longer nucleic acid molecules. In some embodiments, a N-mer barcode sequence comprises 4N complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and WO2019199579A1, which are hereby incorporated by reference in their entirety.

In some embodiments, this disclosure features methods and systems for determining sequences of barcodes that are part of capture probes in an array of features. In some embodiments, the adaptor region that hybridizes to the anchor is a constant sequence. In some embodiments, one or more capture probes include a barcode, a constant sequence, and a capture domain. For example, a capture probe can include, from 5' to 3', a constant sequence, a barcode, and a capture domain. In another sample, a capture probe can include from 5' to 3' a barcode, a constant sequence, and a capture domain. In some embodiments, the capture probe also includes a UMI. For example, a capture probe can include from 5' to 3' a constant sequence, a barcode, a UMI, and a capture domain. In another example, a capture probe can include, from 5' to 3' a barcode, a constant sequence, a UMI, and a capture domain.

In some embodiments, the capture probe comprises a constant sequence in an interior portion of the barcode, wherein the barcode comprises a first portion flanking one side of the constant sequence and a second portion flanking the other side of the constant sequence. In some embodiments, the second portion can be referred to as the "second region of interest" or the "second portion." In some embodiments, the first portion can be referred to as the "first region of interest" or the "first portion." In some embodiments, the second region of interest is 5' of the constant sequence and the first region of interest is 3' of the constant sequence. In some embodiments, the second region of interest is 3' of the constant sequence and the first region of interest is 5' of the constant sequence.

In some embodiments, one or more capture probes include from 5' to 3' a second region of interest, a constant sequence, a second portion of the barcode, and a capture domain. In some embodiments, the capture probe also includes a UMI. In some embodiments, the capture probes also includes a cleavage domain. For example, a capture probe can include from 5' to 3' a cleavage domain, a second region of interest, a constant sequence, a second portion of the barcode, a UMI, and a capture domain.

In some embodiments, a capture probe includes a constant sequence. As used herein, a "constant sequence" refers to a sequence that is identical for all capture probes within a plurality of capture probes. For example, for an array including a plurality of capture probes, the constant sequence can be identical for all capture probes. In some embodiments, the capture probes can have constant sequences that are at least 70% identical (e.g., at least 75% identical, at least 80% identical, at least 85% identical, at least 90% identical, at least 95% identical, or at least 99% identical) to other constant sequences within the array.

III. Bi-Directional In Situ Assays

In some aspects, provided herein are methods for analyzing a first region of interest and a second region of interest of a target nucleic acid, wherein the first region of interest and second region of interest are non-overlapping regions flanking an adaptor region. In some embodiments, the method comprises ligating one or more detection probes to an end of an anchor that hybridizes to an adaptor region of a target nucleic acid, and extending the other end of the anchor using a polymerase in the opposite direction. In some embodiments, the ligation reaction(s) and the extension reaction(s) proceed in opposite directions of the target nucleic acid (e.g., a single-stranded polynucleotide), optionally starting with a common anchor molecule and proceeding in opposite directions. In some embodiments, the ligation reaction(s) and the extension reaction(s) are not performed on (and/or performed to analyze) overlapping sequences. For instance, the target nucleic acid is not circular and the reactions starting with a common anchor molecule hybridized to the target nucleic acid do not resulting in detection of overlapping sequences. In some embodiments, the method comprises using sequencing-by-synthesis (SBS) and sequencing-by-ligation (SBL) from opposite ends of the anchor, thereby determining the sequences of the first and second region of interest. Also provided herein, are methods that includes decoding a barcode using sequencing-by-synthesis and sequencing-by-ligation, capturing an analyte from a biological sample, and using the decoded barcode to determine the location of the analyte in the biological sample based on the location of the decoded barcode.

(a) Anchor, Probes, and Regions of Interest

In some aspects, provided herein are anchor oligonucleotides for use in the methods described herein. In some embodiments, the anchor comprises one, two, or more molecules. In some embodiments, one, two, or more molecules of the adaptor can be ligated together (e.g., using the nucleic acid comprising the adaptor region as a template). In some embodiments, the anchor is between or between about 5 and 50 nucleotides in length, between or between about 5 and 40 nucleotides in length, between or between about 5 and 30 nucleotides in length, between or between about 5 and 20 nucleotides in length, between or between about 10 and 25 nucleotides in length, or between or between about 20 and 35 nucleotides in length.

In some embodiments, the anchor binds to an adaptor region of a target nucleic acid, such as any one of the target nucleic acids described in Section II. In some embodiments, the adaptor region is between or between about 5 and 50 nucleotides in length, between or between about 5 and 40 nucleotides in length, between or between about 5 and 30 nucleotides in length, between or between about 5 and 20 nucleotides in length, between or between about 10 and 25 nucleotides in length, or between or between about 20 and 35 nucleotides in length. In some embodiments, the adaptor region can be a "constant sequence," e.g., a sequence that is common among multiple target nucleic acids, and the same anchor can be used to analyze multiple different regions of interest. In some embodiments, adaptors having a common or "constant" sequence can be used to analyze multiple first and second regions of interest located on the same molecule, using an anchor having the same sequence to analyze multiple first and second regions.

In some embodiments, the adaptor region is flanked by a first region of interest and a second region of interest (e.g., a first portion of an barcode and a second portion of a barcode). The first region of interest and second region of interest can be non-overlapping and non-adjacent (i.e., separated by the adaptor region). In some embodiments, the first region of interest and the second region of interest can be on separate nucleic acid molecules. In some embodiments, the first region of interest, the adaptor region, and the second region of interest are in the same molecule. In some embodiments, the first region of interest and the second region of interest are in a first and a second molecule, respectively. In some embodiments, the first and second molecules hybridize to each other. For example, the first region of interest may be comprised by a first target nucleic acid molecule, and the second region of interest may be on a probe hybridized to the first target nucleic acid molecule (e.g., a padlock probe). In some embodiments, a portion of the adaptor region may be comprised by a probe hybridized to the first target nucleic acid molecule (e.g., a padlock probe). In some embodiments wherein the first and second regions of interest are comprised by first and second nucleic acid molecules, the first and second molecules can be ligated to each other using the anchor as a template.

In some aspects, provided herein are detection probes for determining a sequence of the first region of interest in a sequencing-by-ligation reaction. In some embodiments, the detection probes comprise a sequence of formula $N_xB_yN_z$, wherein N is a degenerate base and B is an interrogatory base, x, y, and z are integers independent of each other, wherein x is 0 or greater, y is 1 or greater, and z is 0 or greater, optionally wherein y is 1 or 2 and (x+z) is at least 4. In some embodiments, the interrogatory region of each detection probe is a single nucleotide, a di-nucleotide, or longer interrogatory nucleotide sequence. In some embodiments, each detection probe comprises a degenerate sequence in addition to the interrogatory region. In some embodiments, the detectable label of each detection probe corresponds to a nucleotide or sequence in the interrogatory region. In some embodiments, the plurality of detection probes comprise detection probes labeled with different detectable labels corresponding to the interrogatory region of each detection probe. In some embodiments, the detectable label of each detection probe is cleavable. In some embodiments, the detectable label is cleaved from the detection probe ligated to the anchor after the detecting step. In some embodiments, all or a portion of the detection probe ligated to the anchor is cleaved and/or unhybridized from the nucleic acid after signal detection. In some embodiments, the detection probe is blocked at the end that is not ligated to the anchor. In some embodiments, the detection probe ligated to the anchor is cleaved to regenerate an end for ligation.

In some embodiments, the adaptor region (e.g., the constant sequence) includes a sequence that is used for initiating a sequencing reaction. For example, an anchor (e.g., the sequencing anchor) or a sequencing primer can bind to the constant sequence. In some embodiments, the constant sequence includes a sequence that is complementary to an anchor. For example, the anchor has sufficient complementarity with the constant sequence for a sequencing-by-ligation reaction. In another example, the anchor has sufficient complementarity with the constant sequence for a sequencing-by-synthesis reaction. In some embodiments, the anchor is at least at least 70% identical (e.g., at least 75% identical, at least 80% identical, at least 85% identical, at least 90% identical, at least 95% identical, or at least 99% identical) to the complementary sequence of the constant sequence.

In some embodiments, the first region of interest and/or second region of interest is a barcode or a portion thereof. In some embodiments, the barcode (e.g., the first portion of the barcode and/or the second portion of the barcode) typically includes 3 or more (e.g., 4 or more, 5 or more, 6 or more, 7 or more, 8 or more, 9 or more, 10 or more, 11 or more, 12 or more, 13 or more, 14 or more, 15 or more, 20 or more) nucleotides. In some embodiments, the barcode (e.g., the first portion of the barcode and/or the second portion of the barcode) includes between 5 and 15 (e.g., between 6 and 12, between 6 and 10) nucleotides.

In some embodiments, the first region of interest (e.g., the barcode or portion thereof) can include n nucleotides (where n corresponds to the number of nucleotides), and the complete sequence of the first region of interest, or complete portion of barcode, can be determined by sequentially hybridizing n different detection probes to the first region of interest, in which case the first region of interest (e.g., barcode) sequence is determined stepwise, one nucleotide at a time. In some embodiments, the complete sequence of the first region of interest, or barcode or portion thereof, can be determined by sequentially hybridizing fewer than n different detection probes to the first region of interest (e.g., the barcode). In some embodiments, at least one of the detection probes, or more than one of the detection probes, determines more than one nucleotide of the first region of interest. In some embodiments, the second region of interest (e.g., the barcode or portion thereof) can include n nucleotides (where n corresponds to the number of nucleotides in the second region of interest), and the complete sequence of the second region of interest (e.g., the barcode or portion thereof) can be determined by sequentially hybridizing n different nucleotide derivatives to the second region of interest (e.g., the barcode or portion thereof), in which case the sequence of the second region of interest (e.g., the barcode or portion thereof) is determined stepwise, one nucleotide at a time.

In some embodiments, all or a portion of the sequence of the first region of interest is determined prior to determination of all or a portion of the sequence of the second portion of the barcode. In some embodiments where sequence of the first region of interest is determined using any of the methods described herein, the anchor is not removed prior to determining all or a portion of the sequence of the second region of interest. For example, the methods described herein can be repeated until the sequence of the first region of interest is determined without having to remove the anchor. In other embodiments, the anchor, extended anchor, ligation product comprising the anchor, or extended ligation product can be stripped and the anchor can be re-hybridized for additional rounds of sequencing.

In some embodiments, the first region of interest is one or more, 2, or more, 3 or more (e.g., 4 or more, 5 or more, 6 or more, 7 or more, 8 or more, 9 or more, 10 or more, 11 or more, 12 or more, 13 or more, 14 or more, 15 or more, 20 or more) nucleotides in length. In some embodiments, first region of interest includes between 5 and 15 (e.g., between 6 and 12, between 6 and 10) nucleotides in length.

In some embodiments, the second region of interest is one or more, 2, or more, 3 or more (e.g., 4 or more, 5 or more, 6 or more, 7 or more, 8 or more, 9 or more, 10 or more, 11 or more, 12 or more, 13 or more, 14 or more, 15 or more, 20 or more) nucleotides in length. In some embodiments, second region of interest includes between 5 and 15 (e.g., between 6 and 12, between 6 and 10) nucleotides in length.

In some embodiments, all or a portion of the sequence of the second region of interest is determined prior to determination of all or a portion of the sequence of the first region of interest. In some embodiments where the second portion of the barcode is determined using any of the methods described herein, the anchor is not removed prior to determining all or a portion of the sequence of the first portion of the barcode. For example, the methods described herein can be repeated until the sequence of the second portion of the barcode is determined without having to remove the anchor. In other embodiments, the anchor, extended anchor, ligation product comprising the anchor, or extended ligation product can be stripped and the anchor can be re-hybridized for additional rounds of sequencing.

In some embodiments, a portion of the sequence of the second region of interest can be determined, followed by a portion of the sequence of the first region of interest, and this process can be repeated until all or substantially all of the sequences of the first and second regions of interest have been determined. In some embodiments, this process can be repeated until the sequence of the first region of interest and the sequence of the second region of interest have been determined without having to remove the anchor. In other embodiments, the anchor, extended anchor, ligation product comprising the anchor, or extended ligation product can be stripped and the anchor can be re-hybridized for additional rounds of sequencing.

(b) Sequencing-by-Ligation

In some embodiments, provided herein are methods including a sequencing-by-ligation (SBL) reaction. In some embodiments of any of the methods for decoding a barcode described herein, the method includes sequencing-by-ligation reaction. In some examples, the SBL reaction includes contacting the sample with a plurality of detection probes, wherein each detection probe comprises an interrogatory region and a detectable label, and is configured to hybridize to the nucleic acid adjacent to an end of the anchor; ligating a detection probe complementary to the first region of interest to the end of the anchor to generate a ligation product; and detecting a signal associated with the detectable label of the ligation product.

Sequencing-by-ligation protocols and other sequencing methods have been described, for example, in WO2020/056381, and U.S. Pat. Nos. 6,306,597, 7,906,285, and 9,404,155, the contents of which are herein incorporated by reference in their entirety. In traditional sequencing-by-ligation (SBL), for example, three mismatched interrogating (or "sequencing") probes and one correctly matched interrogating probe compete for the same ligation site. The difference in their $T_m$ is generally ~1-2° C., enabling them to equilibrate freely depending on the reaction temperature. The three mismatched interrogating probes and one correctly matched interrogating probe can have different $T_m$ temperatures based on the presence or absence of a matching nucleotide. The level of probe hybridization is a function of probe Tm, which is a function of their length; while the slight difference in the probe melting temperature can be used to discriminate alleles (i.e. allele-specific PCR, allele-specific FISH), the fraction of correctly hybridized probes vary dramatically even with small changes in the reaction temperature. However, in some examples the slight difference in the hybridization rate is insufficient to discriminate individual bases with high specificity. Without being bound by theory, the use of ligase can increase the specificity of the method because the ligase is slow to ligate nicked DNA strands if it recognizes a base-pair mismatch. This dramatically improves the specificity of allele discrimination. Thus, sequencing-by-ligation can involve competitive ligation, rapid equilibration of competing probes, and large difference between correct and mismatched probe ligation, enabling specific determination of a sequence in a region of interest. Numerous variations of sequencing-by-ligation are possible and can be used in a method disclosed herein.

In some embodiments, SBL detection probes are labelled with an optical label. In other embodiments, SBL detection probes comprise alternative labels, such a barcode label that allows discrimination of SBL detection probes using probe hybridization, antibody-based detection, or any other means of affinity-based detection.

In some embodiments, SBL detection probes comprise cleavable terminators. Cleavable terminators can prevent simultaneous ligation of multiple SBL probes on repetitive sequences. Cleavable terminators can include, for example, Endonuclease V-based cleavage of DNA. Endonuclease V cuts the DNA 2 or 3 bases away from inosine; therefore, phosphorothioate groups can be added to define the cleavage site at a desired position. This results in efficient cleavage of the terminator to generate a cleaved fragment, which optionally comprises the detectable label.

In some embodiments, the ligase is capable of performing RNA-splinted ligation. In some embodiments, the ligase is a PBCV ligase (e.g., *Chlorella* Virus PBCV-1). In some embodiments, the ligase is T4 Rnl2. In some embodiments, the ligase is a T4 DNA ligase.

In some embodiments, the capture probe is then contacted with a composition that includes multiple different detection probes. In some embodiments, the detection probes are of the same length, but include different nucleotides in at least one non-degenerate position in each sequence. FIG. 2B is a schematic diagram that shows one example of a sequencing procedure that can be used to determine the sequence of a first region of interest (e.g., a second portion of a barcode).

In some embodiments, as seen in FIG. 2B, the composition includes multiple pluralities of detection probes, each having a different nucleotide in the first 3' sequence position of the detection probe, and degenerate bases in the remaining positions. In some embodiments, the position within the nucleotide sequence that includes a known nucleotide and not a degenerate base can be referred to as the "3' sequence position." In some embodiments, the 3' sequence position is the first nucleotide at the 3' end of the detection probe. In some embodiments, the 3' sequence position is the second nucleotide from the 3' end of the detection probe. In some embodiments, the 3' sequence position includes the first two nucleotides adjacent from the 3' end of the detection probe. In some embodiments, the 3' sequence position is at position 3, 4, 5, 6, 7, 8, 9, or 10 from the 3' end of the detection probe (e.g., sequencing probe). For example, when the 3' sequence position is at position 3 from the 3' end of a sequencing probe, the detection probe can have a sequence including, without limitation, 3'-NNXNNNNN-5', where X is the non-degenerate base (e.g., A, G, C, T or U) and where N represents the degenerate bases (e.g., universal bases). In some embodiments, the detection probe that is complementary to the barcode at the non-degenerate position is ligated to the anchor (e.g., the sequencing anchor), and hybridizes to the barcode (e.g., the second portion of a barcode). The non-hybridized detection probes are removed (e.g., removed using a washing step). In some embodiments, an image of the label of the hybridized detection probe is obtained. Non-limiting examples of the label include an optical label, a radioactive label, a fluorescent label, an enzymatic label, a chemiluminescent label, a bioluminescent label, a dye, or any of the other optical labels described herein. The image of the label provides a spatial location of the first label in the image relative to other capture probes (e.g., capture probes attached to features) of the array. In some embodiments, because the first label (e.g., any of the exemplary labels described herein) corresponds to the location of the capture probe and the feature to which it is attached, the feature is then associated with a location in the array, e.g., by reference to the feature's location relative to a reference location such as a fiducial mark or another mark associated with the array. In some embodiments, the feature location corresponds to the label location in the array, as determined from the image.

In some embodiments, each plurality of detection probe in the composition has a different label (e.g., any of the exemplary labels described herein), therefore, the measurement of spectrally resolved absorption or emission of radiation from the hybridized detection probe reveals the identity of the nucleotide at the non-degenerate position (e.g., the 3' sequence position) in the sequencing probe's sequence. In some embodiments, the nucleotide at the non-degenerate position(s) (e.g., the 3' sequence position) of the hybridized detection probe is complementary to the nucleotide at the corresponding location in the second portion of the barcode. In some embodiments, one nucleotide of the second portion of the barcode is determined by identifying the complement of the nucleotide at the non-degenerate position (e.g., the 3' sequence position) of the sequencing probe. For example, the label associated with the detection probe reveals the identity of the nucleotide at the corresponding location in the second portion of the barcode sequence.

In some embodiments, after hybridizing a first detection probe to the capture probe, the capture probe can then be contacted with successive compositions of detection probes (e.g., a composition of multiple different detection probes). In some embodiments, each successive composition of detection probes includes detection probes that include a known nucleotide at a 3' sequence position and a known label (e.g., any of the exemplary labels described herein), where the label is associated with the nucleotide at the 3' sequence position. Therefore, in the successive composition of detection probes, each label is associated with an identified type or plurality of nucleotide at the 3' sequence position of a sequencing probe.

In some embodiments, each successive composition includes detection probes each having a known nucleotide in one or more non-degenerate positions (e.g., 3' sequence position(s)), and degenerate bases in the remaining positions. For example, an additional detection probe that hybridizes to the barcode (e.g., the second portion of the barcode) can include a known nucleotide in the second position from the 3' end, and degenerate bases in the remaining positions. In this case, the known nucleotide in the second position is a complement of a nucleotide in the second portion of the barcode. The other detection probes in the composition that do not hybridize to the barcode can include a known nucleotide at the second position, but the known nucleotide is not a complement of the second portion of the barcode. In some embodiments, at least one nucleotide of the second portion of the barcode is determined by identifying the complement of the known nucleotide at the second position from the 3' end of the additional detection probe (e.g., the 3' sequence position). In some embodiments, exposure of the capture probe and its barcode (e.g., the second portion of the barcode) to successive compositions (e.g., composition of multiple different detection probes) allows step-wise determination of the sequence of the barcode (e.g., the second portion of the barcode).

In some embodiments, as seen in FIG. 2B, among the composition of detection probes, the nucleotide sequences differ at only a single non-degenerate nucleotide position. In some embodiments, the sequencing probes in the composition of detection probes differ at two (or more) non-degenerate positions. In some embodiments, the two non-degenerate positions are adjacent or are non-adjacent in the sequences of the detection probes, and consequently, the sequence of the barcode (e.g., the second portion of the barcode) can be determined at sequential or non-sequential positions using such compositions of detection probes.

In some embodiments, the sequencing-by-ligation steps can be repeated for multiple features in an array, to determine sequences of capture probes linked to each of the multiple features, and to associate each of the multiple features with a different spatial location in the array, relative to one or more reference locations such as fiducial marks. In some embodiments, the sequences of the oligonucleotides (e.g., capture probes) at a particular location of the sample is not known prior to the decoding (e.g., using any of the bi-directional sequencing methods provided herein). In some cases, the array is a bead array (e.g., randomly ordered) contacted with the sample. In some embodiments, each bead is associated with a plurality of oligonucleotides that can be decoded (e.g., using any of the bi-directional sequencing methods provided herein).

In some embodiments, sequencing-by-ligation is repeated until substantially all of the barcode (e.g., the second portion of the barcode) has been decoded. In some embodiments, only a portion of the barcode (e.g., the second portion of the barcode) is determined. For example, to uniquely distinguish among the barcodes (e.g., the second portion of the barcode) of the capture probes in the array, it may be sufficient to determine only a portion of the complete sequence of each barcode (e.g., the second portion of the barcode). Accordingly, the sequencing process can be terminated when a sufficient portion of each barcode (e.g., the second portion of the barcode) has been sequenced to unambiguously distinguish the barcodes from one another.

In some embodiments, after each detection probe has been hybridized and the sequence of a portion of the barcode (e.g., the second portion of the barcode) determined, the hybridized detection probe can be removed via cleavage (e.g., cleavage by any of the exemplary methods described herein or known in the art). For example, the detection probe can be removed using a nuclease (e.g., any of the exemplary nuclease described herein or know in the art). In some embodiments, a detection probe (e.g., any of the exemplary detection probes described herein) includes a nuclease recognition site. In some embodiments, cleavage of the detection probe removes the probe entirely from the barcode (e.g., the second portion of the barcode). In some embodiments, cleavage of the detection probe removes only a first portion of the sequencing probe, and leaves a second portion of the detection probe hybridized to the barcode (e.g., the second portion of the barcode). In some embodiments, provided the second portion of the probe provides an appropriate ligation site, a successive detection probe can be ligated to the remaining second portion of the probe, and can hybridize to the barcode (e.g., the second portion of the barcode) to extend the sequencing procedure. In some embodiments, the removed first portion of the detection probe includes the label.

In some embodiments, determining the sequence of substantially all of the second region of interest (e.g., the second portion of the barcode) includes sequentially hybridizing three or more (e.g., four or more, five or more, six or more, eight or more, ten or more, 12 or more, 15 or more, 20 or more) detection probes to the second region of interest (e.g., the second portion of the barcode), each of which determines a portion of the second region of interest sequence. In some embodiments, successively hybridized detection probes have the same sequence length. In some embodiments, successively hybridized detection probes have different lengths. For example, for a barcode sequence of length n as described above, a hybridized detection probe can be from one nucleotide in length to any length, including lengths of n nucleic acids or more.

In some embodiments, successive detection probes are used to determine the sequence of the second region of interest (e.g., the second portion of the barcode) at successive positions in the sequence. For example, the first detection probe determines the second region of interest (e.g., the second portion of the barcode) sequence at the first position, the additional detection probe determines the second region of interest (e.g., the second portion of the barcode) sequence at the second position, and so on in consecutive fashion. In some embodiments, the sequence of the second region of interest (e.g., the second portion of the barcode) is determined at least partly at non-successive locations. The locations at which the sequence is determined can be selected, for example, based on the compositions of the detection probes and the non-degenerate sequence positions for the probes in a particular composition.

In some embodiments, the sequencing methodology described above can generally be implemented in a variety of different ways. In some embodiments, an anchor binds to the adaptor region (e.g., the constant sequence of a capture probe) and enables a sequencing-by-ligation reaction. In some embodiments, the sequencing-by-ligation reaction relies in part on the ligation of a detection probe to provide either the 5' phosphate or the 3' OH of an anchor.

In some embodiments, the anchor includes a free 5' phosphate that serves as a substrate for a ligation reaction. In some embodiments, the 3' OH is provided by the detection probe. In some embodiments, the anchor includes a free 5' phosphate that can be dephosphorylated by any variety of phosphatases described herein or known in the art (e.g., shrimp alkaline phosphatase (rSAP), calf intestinal phosphatase (CIP), or Antarctic phosphatase (AnP)). In some embodiments, the anchor does not include a free 5' phosphate group. In such cases, the 5' phosphate can be provided by any variety of kinases described herein or known in the art (e.g., T4 polynucleotide kinase). In some embodiments, an anchor includes a 3' OH that serves as a substrate for a ligation reaction. In some embodiments, the 5' phosphate is provided by a detection probe.

In some embodiments, an anchor has a sequence that is n−1 bases different from the original sequence anchor. For example, an anchor having a sequence of 3'-

(SEQ ID NO: 1)
ACTGTCCGATAGTTAGACTG-5' can have an n−1 sequence of 3'-

(SEQ ID NO: 2)
ACTGTCCGATAGTTAGACT-5', where the 5' G is removed. In cases where the sequence to be determined is located 5' to the anchor, the nucleotides to be removed in an n−1 anchor will be removed from the 5' of the anchor. In some embodiments, the anchor is n−1 bases different from the original anchor but includes an additional one or more bases. For example, the anchor that is n−1 of the original anchor includes a nucleotide that is immediately 3' of the original constant sequence (e.g., the base is complementary to the base immediately 5' to the constant sequence in the capture probe). In some embodiments where the sequence to be determined is located 3' to the anchor, the nucleotides to be removed in an n−1 anchor will be removed from the 3' end of the anchor.

In some embodiments, an anchor has a sequence that is n−2 bases different from the original anchor. For example, an anchor having a sequence of 3'-

(SEQ ID NO: 1)
ACTGTCCGATAGTTAGACTG-5' can have an n−2 sequence of 3'-

(SEQ ID NO: 3)
ACTGTCCGATAGTTAGAC-5', where the 5' TG is removed. In cases where the sequence to be determined is located 5' to the anchor, the nucleotides to be removed in an n−2 anchor will be removed from the 5' of the anchor. In some embodiments, the anchor is n−2 bases different from the original anchor but includes an additional one or more bases. For example, the anchor that is n−2 of the original anchor includes one or more nucleotides that are immediately 3' of the original constant sequence (e.g., the one or more bases are complementary to the bases immediately 5' to the constant sequence in the capture probe). In some embodiments, where the sequence to be determined is located 3' to the anchor, the nucleotides to be removed in an n−2 anchor will be removed from the 3' end of the anchor.

The detection probes described herein each generally include (1) at least one base pair that is known prior to contacting the capture probe, and (2) a label that corresponds to the identity (e.g., A, G, C, or T) of the at least one base pair having a known sequence. For example, the when a detection probe is complementary to the sequence of the barcode (e.g., the second portion of the barcode) the detection probe will hybridize (e.g., Watson-Crick base pairing) with the barcode (e.g., the second portion of the barcode) and the label (e.g., any of the exemplary labels described herein) will be detectable upon interrogation.

In some embodiments, the detection probes can range in length from 6 nucleotides to about 12 nucleotides, from about 6 nucleotides to about 11 nucleotides, from about 6 nucleotides to about 10 nucleotides, from about 6 nucleotides to about 9 nucleotides, form about 6 nucleotides to about 8 nucleotides, form about 6 nucleotides to about 7 nucleotides, from about 7 nucleotides to about 12 nucleotides, from about 7 nucleotides to about 10 nucleotides, from about 7 nucleotides to about 9 nucleotides, from about 7 nucleotides to about 8 nucleotides, from about 8 nucleotides to about 12 nucleotides, from about 8 nucleotides to about 11 nucleotides, from about 8 nucleotides to about 10 nucleotides, from about 8 nucleotides to about 9 nucleotides, from about 9 nucleotides to about 12 nucleotides, from about 9 nucleotides to about 11 nucleotides, from about 9 nucleotides to about 10 nucleotides, from about 10 nucleotides to about 12 nucleotides, from about 10 nucleotides to about 11 nucleotides, or from about 11 nucleotides to about 12 nucleotides. In some embodiments, the detection probes can be 8 nucleotides in length.

In some embodiments, the detection probes include a known nucleotide sequence located in at least one location within the detection probe (e.g., the location with the known nucleotide is the "3' sequence position"). For example, the detection probe can include a sequence where it is known that an A, G, C, or T is located at the first position in the 3' to 5' orientation sequencing probed. The first position in the 3' to 5' sequence orientation of the detection probe can be an A. The first position in the 3' to 5' sequence orientation of the detection probe can be a G. The first position in the 3' to 5' sequence orientation of the detection probe can be a C. The first position in the 3' to 5' sequence orientation of the detection probe can be a T. In cases where the first position of the detection probe includes a known sequence, the remaining nucleotides include a degenerate sequence (e.g., universal bases).

In some embodiments, the detection probe can include a sequence where it is known that an A, G, C or T is located at the second position in the 3' to 5' orientation of the detection probe (e.g., the second position is the "3' sequence position"). For example, the second position in the 3' to 5' sequence orientation of the detection probe can be an A. The second position in the 3' to 5' sequence orientation of the detection probe can be a G. The second position in the 3' to 5' sequence orientation of the detection probe can be a C. The second position in the 3' to 5' sequence orientation of the detection probe can be a T. In cases where, the second position of the detection probe includes a known sequence, the remaining nucleotides include a degenerate sequence (e.g., universal bases).

In some embodiments, the detection probe can include a sequence where it is known that an A, G, C, or T is located at the first position in the 5' to 3' orientation of the detection probe (e.g., the first position is the "5' sequence position"). The first position in the 5' to 3' sequence orientation of the detection probe can be an A. The first position in the 5' to 3' sequence orientation of the detection probe can be a G. The first position in the 5' to 3' sequence orientation of the detection probe can be a C. The first position in the 5' to 3' sequence orientation of the detection probe can be a T. In cases where the first position of the detection probe includes a known sequence, the remaining nucleotides include a degenerate sequence (e.g., universal bases).

In some embodiments, the detection probe can include a sequence where it is known that an A, G, C or T is located at the second position in the 5' to 3' orientation of the detection probe (e.g., the second position is the "5' sequence position"). For example, the second position in the 5' to 3' sequence orientation of the detection probe can be an A. The second position in the 5' to 3' sequence orientation of the detection probe can be a G. The second position in the 5' to 3' sequence orientation of the detection probe can be a C. The second position in the 5' to 3' sequence orientation of the detection probe can be a T. In cases where, the second position of the detection probe includes a known sequence, the remaining nucleotides include a degenerate sequence (e.g., universal bases).

In some embodiments, where a detection probe includes a first known nucleotide at a first position (e.g., the first nucleotide at the 3' end or first nucleotide at the 5' end) and a second known nucleotide at a second position (e.g., the second nucleotide from the 3' end or second nucleotide at the 5' end), there are 16 possible dinucleotide combinations. For example, the 16 possible dinucleotide combinations include: TA, CG, GC, TA, AC, AA, GA, CA, CC, TC, GT, GG, AG, TG, TT, and CT. In such cases, the dinucleotide combination at known location in the detection probe can be referred to collectively as the 3' sequence position.

In some embodiments, the detection probe can include a sequence where it is known that an A, G, C, or T is present at any of the positions in a 3' to 5' orientation (e.g., any of the positions with the known nucleotide is the "3' sequence position"). In some embodiments, the detection probe can include a sequence where it is known that an A, G, C, or T is present at any of the positions in a 5' to 3' orientation.

In some embodiments, the nucleotides included in a detection probe and/or an anchor can be non-natural nucleotides, modified nucleotides (e.g., 5' Methyl group, 2' Fluoro) or any of a variety of different nucleotides that can facilitate the sequencing methods described above. Additional examples of such nucleotides have been described previously.

In some embodiments, some or all of the sequencing steps described above can be implemented using ABI SOLID v2.0 sequencing chemistry. The SOLID v2.0 sequencing chemistry uses a mixture of labeled detection probes and queries the input strand with ligase in order to resolve the sequence of interest. The SOLID v.2.0 chemistry utilizes ½ encoding where the nucleotides at the first two positions of the sequencing primer are known and are associated with a particular fluorescent dye. Each detection probe (numbered from the 3' end) includes universal bases at bases 3-5 and one of sixteen specific dinucleotides at positions 1-2 (e.g., known nucleotide). Positions 6-8 include universal bases and are coupled to one of four fluorescent dyes. In some embodiments, sequencing-by-ligation involves providing an array that includes features comprising at least capture probe having a barcode (e.g., the second portion of the barcode) and contacting the capture probe on the array with an anchor.

In some embodiments where some or all of the sequencing steps described above can be implemented using ABI SOLID v2.0 sequencing chemistry, the anchor is at least partially complementary to the constant sequence and provides a 5' phosphate that can be used as a substrate in a ligation reaction. The capture probes, with the anchor bound, are contacted with a composition of detection probes where the detection probes include a known dinucleotide combination at a 3' sequence position and a known label (e.g., any of the exemplary labels described herein), where the label is associated with the dinucleotide combination at the known 3' sequence position. If the detection probe contains a dinucleotide combination at the 3' end of the detection probe that is complementary to the capture probe (e.g., the second portion of barcode sequence), then a ligation reaction occurs and the detection probe is ligated onto the capture probe. The fluorescent dye (or other optical label) associated with that dinucleotide is detectable upon interrogation. As described herein, the non-selective nature of the universal bases allows ligation where there is complementarity between the dinucleotides and the second portion of the barcode.

In some embodiments where some or all of the sequencing steps described above can be implemented using ABI SOLID v2.0 sequencing chemistry, the anchor is complementary to the constant sequence and provides a 3' OH that can be used as a substrate in a ligation reaction. The capture probes, with the anchor bound, are contacted with a composition of detection probes, where the detection probes include a known dinucleotide combination at a 5' sequence position and a known label (e.g., any of the exemplary labels described herein), where the label is associated with the dinucleotide combination at the known 5' sequence position.

If the detection probe contains a dinucleotide combination at the 5' end of the detection probe that is complementary to the first unpaired dinucleotides of the first region of interest, then a ligation reaction occurs and the detection probe is ligated to the anchor. The fluorescent dye (or other optical label) associated with that dinucleotide is detectable upon interrogation. As described herein, the non-selective nature of the universal bases allows ligation where there is complementarity between the dinucleotides and the first portion of the barcode.

In some embodiments where some or all of the sequencing steps described above can be implemented using ABI SOLiD v2.0 sequencing chemistry, before detection of the fluorescent dye or other label (e.g., any of the exemplary labels described herein), un-bound detection probes are washed away and un-extended fragments are capped and treated with phosphatase (e.g., any of the exemplary phosphatases described herein) to prevent un-extended strands from contributing to out of phase ligation events. After one or more images of the nucleic acid being sequenced (e.g., of the tissue sample or array comprising the nucleic acid) have been obtained to obtain fluorescence or other optical information that can be used to identify dinucleotide combinations during sequencing, the fluorescent dye (or other optical label) is removed using a two-step chemical cleavage of the three 5' bases or three 3' bases of the detection probe that leaves behind a sequencing probe, including the five most 3' bases or five most 5' bases of the original sequence, which includes a 5' phosphate or a 3' OH.

In some embodiments where some or all of the sequencing steps described above can be implemented using ABI SOLiD v2.0 sequencing chemistry, the method is repeated with interrogation focusing on bases 6-7 of the first region of interest (e.g., bases 6-7 of the first portion of a barcode). After the first "repeat" (e.g., two runs through the method), a "reset" is performed wherein the anchor and ligated detection probes are removed from the template. A new anchor that is n−1 nucleotides different than the detection probe used in the first two runs through the method is contacted to the adaptor region. The method is then repeated with the same composition of detection probes, wash, detection, and cleaving steps performed until all or a portion of the sequence of the region of interest (e.g., the first region of interest) is determined. In some embodiments where the sequence of a barcode (e.g., the first portion of the barcode) is determined, the method as described herein can be used. In some embodiments, the use of four fluorescent dyes or other distinguishable labels (e.g., any of the exemplary labels described herein) means there are four dinucleotide combinations for each label. In order to resolve the sequence of interest following hybridization of these detection probes, dibase encoding is used to base call the template sequence (see Applied Biosystems, "Application Note: Principles of Di-Base Sequencing and the Advantages of Color Space Analysis in the SOLiD System" (2008), the entire contents of which are incorporated herein by reference).

In some embodiments, the detection probe includes universal bases. As used herein, a "universal base" refers to a nucleobase analog that can hybridize non-selectively to each of the native bases (e.g., A, C, G, or T). (See Berger et al., *Nucleic Acid Res.*, 28(15): 2911-2914 (2000), the entire contents of which are incorporated herein by reference.

A detection probe that includes a sequence of 3'-ANNNNNNN-5', where A is a known nucleotide at a first position (e.g., the 3' sequence position) and N represents a universal base or degenerate base located at positions two through eight, will hybridize to a complement sequence only when a T is at the first position on the 5' end (e.g., 5'-TNNNNNNN-3'. The non-selective nature of the universal bases allows ligation where there is complementarity between the known one or more nucleotides and the complementary strand (e.g., barcode sequence). In some embodiments, where there are there are two known nucleotides in the sequence, ligation occurs between the detection probe and the complementary sequence when there is complementarity between the two known nucleotides and the two corresponding nucleotides in the complementary sequence. In some embodiments, all of the N bases are universal bases. In some embodiments, all of the N bases are degenerate bases. In some embodiments, the N bases can be a mix of one or more degenerate nucleotides and one or more universal nucleotides. The number of N bases included in a detection probe can vary, e.g., from one to 10 nucleotides, 2 to 8 nucleotides, 2 to 6 nucleotides, or 2 to 4 nucleotides.

In some embodiments, the sequencing procedure includes a removing step where the detection probe is cleaved. Cleavage can result in the release of the portion of the detection probe that does not contain complementarity with the barcode (e.g., the sequence of the detection probe that includes universal bases). In some embodiments, complementarity between the detection probe and the barcode occur either at the first one or two nucleotides at the 3' end of the detection probe or at the first one or two nucleotides at the 5' end of the sequencing probe. For example, when the sequence of interest is downstream (3') of the constant sequence on the barcode and an anchor is hybridized to the constant sequence, the anchor can provide a free 5' phosphate as a substrate for a ligation reaction and the detection probes can provide the 3' OH. In such circumstances, the detection probe will include nucleotides with known sequences at the 3' end of the sequencing probe.

In some embodiments, when a detection probe contains one or two nucleotides at the 3' end that are complementary to the first region of interest, the detection probe can be ligated to the 5' end of the anchor. In this circumstance, cleavage of the detection probe will result in the release (e.g., removal) of the nucleotides at the 5' positions of the sequencing probe. The cleaved detection probe can now serve as a substrate in a new ligation reaction, if following the cleavage step, the detection probe retains a free 5' phosphate.

(c) Sequencing-by-Synthesis

In some embodiments, sequencing-by-synthesis disclosed herein comprises contacting a sample with a polymerase, at least 4 distinguishable, blocked deoxyribonucleotide triphosphate (dNTP) analogue species, at least 3 of which are labeled such that various distinguishable, blocked dNTP analogue species can be distinguished from the other such species, under conditions to allow incorporation of one of the distinguishable, blocked dNTP analogue species using the second region of interest as a template to form blocked extension product(s); and determining the identity of the distinguishable, blocked dNTP analogue incorporated into the blocked extension product(s). Suitable 3' blocked nucleotide analogues and methods of sequencing have been described, for example, in Ronaghi et al., Science, 281:363-365, 1998; Li et al., Proc. Natl. Acad. Sci. USA, 100:414-419, 2003; Metzker, Nat Rev Genet. 11:31-46, 2010; Ju et al., Proc. Natl. Acad. Sci. USA 103:19635-19640, 2006; Bentley et al., Nature 456:53-59, 2008; in U.S. Pat. Nos. 6,210,891, 6,828,100, 6,833,246, 6,911,345, 7,057,026, 7,541,444, 8,241,573, 10,190,162, 10,851,410; and in U.S. Patent Application Pub. Nos. US 2020/0102609 and US 2017/0029883, the contents of which are herein incorporated by reference in their entirety.

In some aspects, methods of SBS comprise the controlled (e.g., one at a time) incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring. In one approach, reversible terminator nucleotides (RTs) are used to determine the sequence of the DNA template. Exemplary reversible terminators and their use in sequencing technologies are review in Chen et al. (2013) *Genomics, Proteomics,& Bioinformatics* 11(1): 34-40, incorporated herein by reference in its entirety. In the most commonly used SBS approach, each RT comprises a modified nucleotide that includes (1) a blocking group that ensures that only a single base can be added by a DNA polymerase enzyme to the 3' end of a growing DNA copy strand, and (2) a fluorescent label that can be detected by a camera. In the most common SBS methods, templates and sequencing primers are fixed to a solid support and the support is exposed to each of four DNA nucleotide analogs, each comprising a different fluorophore attached to the nitrogenous base by a cleavable linker, and a 3'-O-azidomethyl group at the 3'-OH position of deoxyribose, and DNA polymerase. Only the correct, complementary base anneals to the target and is subsequently incorporated at the 3' terminus of primer. Nucleotides that have not been incorporated are washed away and the solid support is imaged. TCEP (tris(2-carboxyethyl)phosphine) is introduced to cleave the linker and release the fluorophores and to remove the 3'-O-azidomethyl group, regenerating a 3'-OH. The cycle can then be repeated (Bentley et al., Nature 456, 53-59, 2008). A different fluorescent color label is used for each of the four bases, so that in each cycle of sequencing, the identity of the RT that is incorporated can be identified by its color.

In other aspects, SBS can comprise the use of nucleotides that are not directly linked to a detectable label. In some embodiments of SBS sequencing methods described herein, the last incorporated nucleotide base is identified by binding of an affinity reagent (e.g., antibody, aptamer, affimer, knottin, etc.) that recognizes the base, the sugar, a cleavable blocking group or a combination of these components in the last incorporated nucleotide. The binding can be directly or indirectly associated with production of a detectable signal. In some embodiments the epitope recognized by the affinity reagent is formed by the incorporated nucleoside itself (that is, the base plus sugar) or the nucleoside and 3' blocking group. In some embodiments the epitope recognized by the affinity reagent is formed by the reversible terminator itself, the reversible terminator in combination with the deoxyribose, or the reversible terminator in combination with the nucleobase or nucleobase and deoxyribose. Suitable affinity agents have been described, for example, in U.S. Pat. No. 10,851,410 herein incorporated by reference.

In some embodiments of the methods for analyzing a nucleic acid described herein, the method includes sequencing-by-synthesis where an anchor is hybridized to an adaptor region of a nucleic acid, and nucleotides or nucleotide derivatives are hybridized to the second region of interest adjacent to the 5' end of the adaptor region. In some embodiments, the method comprises incorporation of nucleotides or nucleotide derivatives into the 3' end of the anchor using a polymerase. In some embodiments, the nucleic acid is contacted with multiple different nucleotide derivatives and a DNA polymerase. In the first SBS reaction, a nucleotide derivative is coupled to the free 3' end of the anchor based on the complementarity of the nucleotide derivative to the first unpaired nucleotide of the second region of interest. In some embodiments, non-hybridized nucleotide derivatives are removed (e.g., washed away). An image is obtained of the label associated with the nucleotide derivative while the nucleotide derivative is hybridized to the first portion of the barcode. Based on the image, the identity of the nucleotide in the second region of interest is determined by identifying the nucleotide derivative in the image based on the label, and identifying the nucleotide in the position of the second region of interest as the complement to the nucleotide derivative coupled to the nucleic acid in the second region of interest.

In some embodiments, a nucleotide derivative includes a nucleic acid and a label. In some embodiments, the nucleotide derivatives include 5' triphosphates of 2'deoxyadenosine, 2'-deoxyguanosine, 2'-deoxycytidine and 2'-deoxythymidine, where each nucleotide derivative comprises a 3' blocking group and an optical label distinguishable from the optical labels of the other nucleotide derivatives. In some embodiments, the nucleotide derivatives include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

Non-limiting examples of the label include an optical label, a radioactive label, a fluorescent label, an enzymatic label, a chemiluminescent label, a bioluminescent label, a dye, or any of the other optical labels described herein. The label is coupled to the nucleotide using any of the methods described herein or known in the art. The image of the label provides a spatial location of the label in the image relative to other features of the sample (e.g., a cell, tissue sample, or array). In some embodiments, because the label corresponds to the location of the nucleic acid to which it is attached, the localization of the nucleic acid in the biological sample can be determined.

In some embodiments, because each type of nucleotide derivative in the composition has a different label (e.g., any of the exemplary labels described herein), the measurement of spectrally resolved absorption or emission of radiation from the hybridized nucleotide derivative reveals the identity of the type of nucleotide derivative hybridized to the second region of interest. In some embodiments, the type of nucleotide derivative is complementary to a nucleic acid in second region of interest, wherein iterative imaging of hybridized nucleotide derivatives reveals the sequence of second region of interest.

In some embodiments, the nucleic acid can then be contacted with successive compositions of nucleotide derivatives in subsequent rounds of sequencing-by-synthesis. Each successive composition can include the nucleotide derivatives including 5' triphosphates of 2'deoxyadenosine, 2'-deoxyguanosine, 2'-deoxycytidine and 2'-deoxythymidine, where each type of nucleotide derivative comprises a 3' blocking group and a label (e.g., any of the exemplary labels described herein) distinguishable from the labels (e.g., any of the exemplary labels described herein) of the other type of nucleotide derivatives. For example, the type of nucleotide derivative that hybridizes to the second region of interest can include a known nucleotide with a known label.

Imaging the label (e.g., any of the exemplary labels described herein) of the second nucleotide derivative reveals the identity of the nucleotide at the corresponding second location in the second region of interest. In this manner, exposure of the nucleic acid comprising the second region of interest to successive compositions allows step-wise determination of the sequence of the second region of interest.

In some embodiments, sequencing-by-synthesis can be performed simultaneously or sequentially for nucleic acid targets in a sample, to determine sequences of second regions of interest in each of the nucleic acids, and to associate the sequence of one or more second regions of interest in each of the nucleic acids with the localization of the corresponding nucleic acids in the sample.

In some embodiments, substantially all of the sequence of the second region of interest is determined. In some embodiments, only a portion of the sequence of the second region of interest is determined. For example, to uniquely distinguish among second regions of interest (e.g., barcodes) of nucleic acids, it may be sufficient to determine only a portion of each region of interest (e.g., a portion of a barcode). Accordingly, the sequencing process can be terminated when a sufficient portion of each region of interest (e.g., the portion of the barcode) has been sequenced to unambiguously distinguish the regions of interest (e.g., barcodes) from one another.

(d) Amplification

Figure 5A:
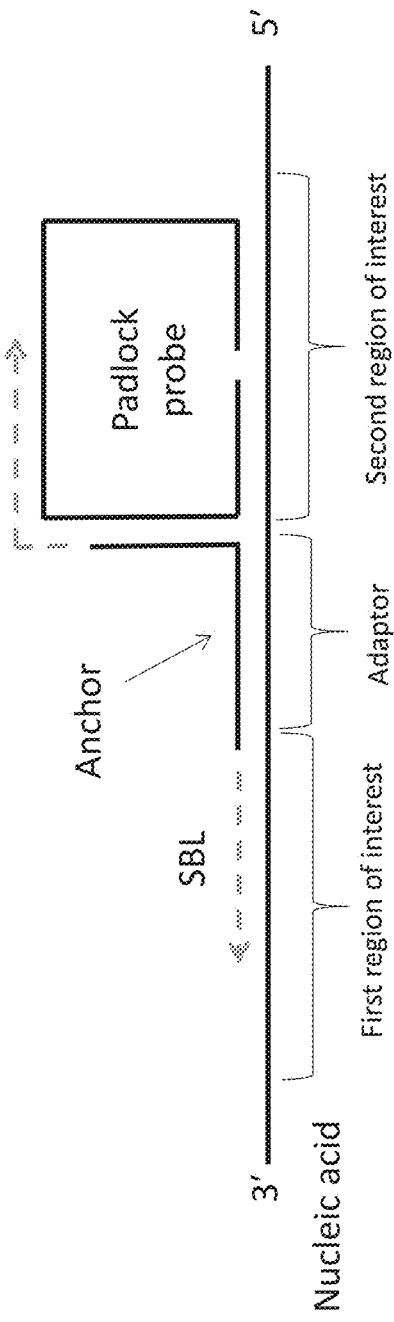
FIGS. 5A-5B show an exemplary embodiment comprising contacting the sample with a primary probe comprising a sequence complementary to the second region of interest; and extending the anchor with a polymerase using the primary probe as a template. The extending step using the polymerase can occur before or after one or more cycles of SBL. The primary probe can be a padlock probe.
Figure 5B:
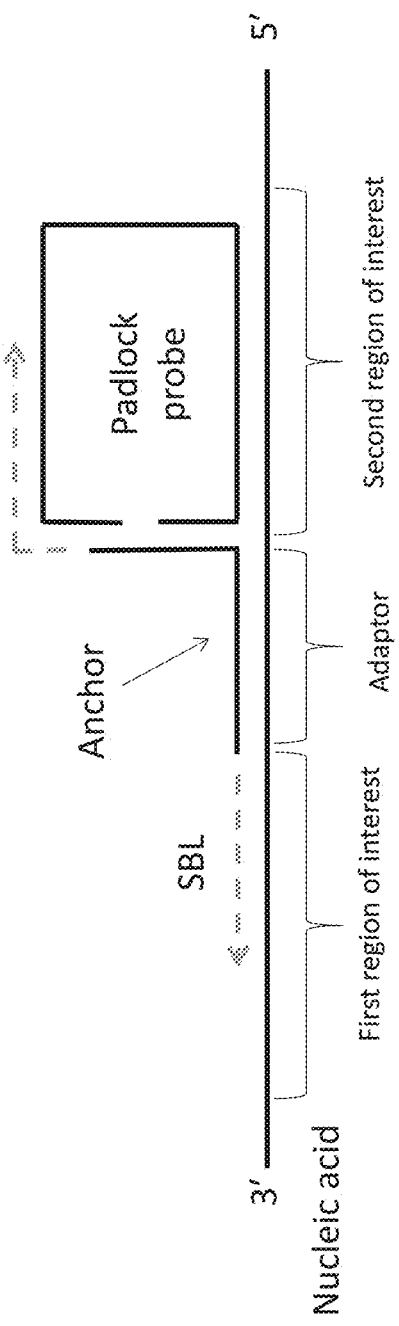

In some embodiments, the methods of the invention comprise the step of extending and/or amplifying one or more polynucleotides, for instance a probe (e.g., a primary probe, a padlock probe, or a detection padlock probe) hybridized to the second region of interest, a circular probe formed from the padlock probe, or the second region of interest of the nucleic acid. In some embodiments, the amplifying is achieved by performing rolling circle amplification (RCA). In some embodiments, the method comprises contacting a target nucleic acid with a primary probe (e.g., padlock probe) and an anchor to form a hybridization complex, wherein the padlock probe hybridizes to the second region of interest. In some embodiments, the anchor comprises a region that hybridizes to the primary probe (e.g., padlock probe or circular probe) for priming of the amplification reaction. In some embodiments, the padlock probe is circularized using the target nucleic acid as a splint, as shown in FIG. 5A. In some embodiments, the padlock probe is ligated and circularized using the anchor or the ligated anchor complex (e.g., following SBL) as a splint, as shown in FIG. 5B. In some embodiments, following ligation and circularization of the padlock probe to form a circular probe, amplification is performed using the circular probe as template and the anchor or ligated anchor complex as a primer. In some embodiments, a sequencing-by-ligation reaction is performed from one end of the anchor (e.g., the 5' end of anchor) and a rolling circle amplification of the circularized padlock probe is performed using the other end of the anchor (e.g., the 3' end) as a primer.

In some embodiments, upon addition of a DNA polymerase in the presence of appropriate dNTP precursors and other cofactors, the anchor is elongated to produce multiple copies of the circular template. This amplification can occur before SBL or after SBL. This amplification step can utilize isothermal amplification or non-isothermal amplification. In some embodiments, after the formation of the hybridization complex and association of the amplification probe, the hybridization complex is rolling-circle amplified to generate an amplicon (e.g., a DNA nanoball) containing multiple copies of the circular template or a sequence thereof. Techniques for rolling circle amplification (RCA) are known in the art such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 November 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:e118, 2001; Dean et al. Genome Res. 1 1: 1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 ((29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects, the modified nucleotides can be employed. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., anchor or amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix.

Exemplary modification and polymer matrix that can be employed in accordance with the provided embodiments comprise those described in, for example, US 2016/0024555, US 2018/0251833, US 2016/0024555, US 2018/0251833 and US 2017/0219465. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

(e) Decoding an Array

In some embodiments of the methods of analyzing a nucleic acid as described herein, the method includes decoding a barcode, e.g., a first portion and a second portion of a barcode flanking an adaptor region, or a first barcode and a second barcode flanking an adaptor region.

Commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina® sequencing (e.g., flow cell-based sequencing techniques), sequencing by synthesis using modified nucleotides (such as commercialized in TruSeq™ and HiSeq™ technology by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, an array is an ordered array or an random array. In some embodiments, an array comprises a plurality of beads as the features in the array. In some embodiments, two or more beads are dispersed onto a substrate to create an array, where each bead is a feature on the array. In some embodiments, the beads are attached to a substrate. For example, the beads can optionally attach to a substrate such as a microscope slide and in proximity to a biological sample (e.g., a tissue section that includes cells). The beads can also be suspended in a solution and deposited on a surface (e.g., a membrane, a tissue section, or a substrate (e.g., a microscope slide)). Beads can optionally be dispersed into wells on a substrate, e.g., such that only a single bead is accommodated per well.

Examples of arrays of beads on or within a substrate include beads located in wells such as the BeadChip array (available from Illumina Inc., San Diego, CA), arrays used in sequencing platforms from 454 LifeSciences (a subsidiary of Roche, Basel, Switzerland), and array used in sequencing platforms from Ion Torrent (a subsidiary of Life Technologies, Carlsbad, CA). Examples of bead arrays are described in, e.g., U.S. Pat. Nos. 6,266,459; 6,355,431; 6,770,441; 6,859,570; 6,210,891; 6,258,568; and 6,274,320; U.S. Pat. Application Publication Nos. 2009/0026082; 2009/0127589; 2010/0137143; 2019/0177777; and 2010/0282617; and PCT Patent Application Publication Nos. WO 00/063437 and WO 2016/162309, the entire contents of each of which is incorporated herein by reference.

In some embodiments, the bead array includes a plurality of beads. For example, the bead array can include at least 10,000 beads (e.g., at least 100,000 beads, at least 1,000,000 beads, at least 5,000,000 beads, at least 10,000,000 beads). In some embodiments, the plurality of beads includes a single type of bead (e.g., substantially uniform in volume, shape, and other physical properties, such as translucence). In some embodiments, the plurality of beads includes two or more types of different beads.

Bead arrays can be generated by attaching beads (e.g., barcoded beads) to a substrate in a regular pattern, or an irregular arrangement. In some embodiments, the barcode sequences are known before attaching them to the substrate. In some embodiments, the barcode sequences are not known before attaching them to the substrate. Beads can be attached to selective regions on a substrate by, e.g., selectively activating regions on the substrate to allow for attachment of the beads. Activating selective regions on the substrate can include activating or degrading a coating (e.g., a conditionally removable coating as described herein) at the selective regions where the coating has been applied on the substrate, rendering the selective regions more permissive to bead attachment as compared to regions outside of the selected regions. The regions that are rendered more permissive for bead attachment can be configured to fit only one bead or multiple beads (e.g., limited by well size or surface patterning, such as fabrication techniques). Beads bound to the selected regions can form a two-dimensional array on the substrate. The substrate can be uniformly or non-uniformly coated with the coating. The beads can be any suitable beads described herein, including beads that are attached to one or more spatial barcodes. Beads can be attached to the selected regions according to any of the methods suitable for attaching beads to substrates described herein, such as through covalent bonds, non-covalent bonds, or chemical linkers.

In some embodiments, barcodes in an array are decoded. Methods of decoding of arrays (e.g., bead arrays) without relying solely on unique optical signatures, e.g., combinatorial decoding of random nucleic acid arrays, are described in U.S. Pat. Nos. 6,620,584, 7,166,431, 7,563,576, 7,960,119, 8,206,917, 8,563,246, and 9,163,283, incorporated herein by reference in their entirety.

In some aspects, provided herein is a method for decoding an array, such as a random array, e.g., a bead array or an array comprising DNA nanoballs. In some embodiments, the method comprises: (a) contacting the array with a plurality of detection probes, wherein: the array comprises a plurality of features each comprising multiple nucleic acid molecules on a substrate, wherein a nucleic acid molecule in a feature comprises non-overlapping first and second regions of interest flanking an adaptor region that hybridizes to an anchor, the first and/or second regions of interest comprises one or more barcode sequences, and each detection probe comprises an interrogatory region and a detectable label, and is configured to hybridize to the nucleic acid molecule adjacent to an end of the anchor; ligating a detection probe complementary to the first region of interest to the end of the anchor to generate a ligation product; and detecting a signal associated with the detectable label of the ligation product; (b) contacting the sample with a pool of nucleotides and/or analogs thereof, thereby incorporating a nucleotide or analog thereof by a polymerase into the other end of the anchor, thereby extending the anchor using the second region of interest as a template to generate an extension product; and detecting a signal associated with the incorporated nucleotide or analog thereof in the extension product, wherein the contacting, ligating, and detecting of detection probes (e.g., steps in (a)) are repeated to determine a sequence of the first region of interest and/or the contacting and detecting of the nucleotides and/or analogs thereof (e.g., steps in (b)) are repeated to determine a sequence of the second region of interest, thereby determining the one or more barcode sequences. In some embodiments, the method includes (c) associating the one or more barcode sequences in the nucleic acid molecules with the locations of the corresponding features in the array, thereby decoding the array.

In some embodiments, the method includes capturing an analyte from a biological sample prior to decoding a barcode. In some embodiments, the method includes capturing an analyte from a biological sample after decoding a barcode. In some embodiments, the barcode (e.g., a first portion and/or a second portion of a barcode) are determined using sequencing-by-synthesis. In some embodiments, the barcode (e.g., a first portion and/or a second portion of a barcode) are determined using sequencing-by-ligation. In some embodiments, the barcode (e.g., a first portion and/or a second portion of a barcode) is determined using sequencing-by-synthesis and sequencing-by-ligation. In some embodiments, a first portion of the barcode is determined using sequencing-by-synthesis and a second portion of the barcode is determine using sequencing-by-ligation. In some embodiments, a first portion of the barcode is determined using sequencing-by-synthesis prior to the second portion of the barcode being determined using sequencing-by-ligation. In some embodiments, a second portion of the barcode is determined using sequencing-by-ligation prior to the first portion of the barcode being determined using sequencing-by-synthesis. In some embodiments, the first and second portion of the barcode are non-overlapping regions flanking the adaptor (e.g., the constant sequence) region.

In some embodiments of the methods of decoding an array as described herein, the method includes providing an array including a plurality of features on a substrate, where a feature of the plurality of features includes a capture probe, where the capture probe includes a barcode, an adaptor region, and a capture domain; determining the sequence of the barcode; capturing an analyte of a biological sample with the capture domain; where determining the sequence of the barcode includes performing sequencing-by-synthesis (e.g., using any of the sequencing-by-synthesis method described herein) on the barcode, thereby decoding the barcode. In some embodiments, the barcode includes an adaptor region in an interior portion of the barcode, where the barcode comprises a first portion and a second portion flanking the adaptor (e.g., the constant sequence) region. In some embodiments, the capture domain can hybridize to a nucleic acid sequence present on or associated with the analyte. In some embodiments, capturing the analyte of the biological sample with the capture domain includes releasing the capture probe from the array and contacting the biological sample with the released capture probe. In some embodiments, the analyte includes DNA or RNA. In some embodiments, the analyte includes a protein.

In some embodiments, performing sequencing-by-synthesis includes contacting a sample (e.g., a tissue sample or array) with nucleotide derivatives; hybridizing a nucleotide derivative to the first region of interest, where the nucleotide derivative includes a label (e.g., any of the exemplary labels described herein) and a nucleic acid; obtaining an image of the label with the nucleotide derivative hybridized to region of interest; determining, based on the image, the sequence of a nucleic acid in the first unpaired position of the region of interest adjacent to the anchor. For example, based on the image, the identity of the hybridized nucleotide in the first region of interest is determined by identifying the nucleotide derivative in the image based on the label of the nucleotide derivative. In some embodiments, the capturing step includes contacting the array with the biological sample and allowing the analyte to interact with the capture probe. In some embodiments, the sequencing-by-synthesis steps are repeated until substantially all of the first region of interest has been analyzed (e.g., decoded).

In some embodiments where the sequence of the second region of interest is determined using sequencing-by-synthesis, the method also includes performing sequencing-by-ligation to determine the sequence of the first region of interest. In some embodiments, performing sequencing by ligation includes ligating a first detection probe to the end of the anchor, wherein the first detection probe includes a label (e.g., any of the exemplary labels described herein) and a nucleotide sequence; obtaining an image of the label with the detection probe hybridized to the barcode; determining, based on the image, one or more nucleotides of the barcode sequence. For example, based on the image, one nucleotide of the second portion of the barcode is determined by identifying the complement of the known nucleotide at the 3' sequence position of the first sequencing probe. In some embodiments, the sequencing-by-ligation steps are repeated until substantially all of the second portion of the barcode has been decoded. In some embodiments, decoding the second portion of the barcode by sequencing-by-ligation occurs prior to, contemporaneously with, or after removing the biological sample from the array.

In some embodiments of the methods for decoding a barcode as described herein, the method includes providing an array including a plurality of features on a substrate, wherein a feature of the plurality of features includes a capture probe, wherein the capture probe includes a barcode, a constant sequence, and a capture domain; determining the sequence of the barcode and associating the feature with a location in the array; capturing an analyte of a biological sample with the capture domain; and determining the location of the captured analyte in the biological sample based on the location of the feature in the array, where determining the sequence of the barcode and associating the feature with the location in the array includes performing sequencing-by-ligation on the barcode, thereby decoding the barcode. In some embodiments the barcode includes a constant sequence in an interior portion of the barcode and the barcode includes a first portion and a second portion. In some embodiments, the capture domain can hybridize to a nucleotide sequence present on or associated with the analyte. In some embodiments, the capturing step includes contacting the array with the biological sample and allowing the analyte to interact with the capture probe. In some embodiments, capturing the analyte of the biological sample with the capture domain includes releasing the capture probe from the array and contacting the biological sample with the released capture probe. In some embodiments, the analyte includes DNA or RNA. In some embodiments, the analyte includes a protein.

In some embodiments, performing sequencing-by-ligation includes ligating a first detection probe hybridized to barcode to the end of an anchor, wherein the first detection probe includes a label (e.g., any of the exemplary optical labels described herein) and a nucleotide sequence; obtaining an image of the label with the detection probe hybridized to the barcode; determining, based on the image, a portion one or more nucleotides of the barcode sequence. For example, based on the image, one nucleotide of the second portion of the barcode is determined by identifying the complement of the known nucleotide at the 3' sequence position of the first sequencing probe. In some embodiments, the sequencing-by-ligation steps are repeated until substantially all of the second portion of the barcode has been decoded. In some embodiments, decoding the barcode by sequencing-by-ligation occurs prior to, contemporaneously with, or after removing the biological sample from the array.

In some embodiments where the second portion of the barcode is decoded using sequencing-by-ligation, the method also includes performing sequencing-by-synthesis to decode the first portion of the barcode. In some embodiments, performing sequencing by synthesis includes contacting an array with nucleotide derivatives; hybridizing a nucleotide derivative to the first portion of the barcode, wherein the nucleotide derivative includes a label (e.g., any of the exemplary labels described herein) and a nucleic acid; obtaining an image of the label with the nucleotide derivative hybridized to the first portion of the barcode; determining, based on the image, the identity of a nucleotide in the first portion of the barcode sequence. For example, based on the image, the identity of the hybridized nucleotide in the first portion of the barcode is determined by identifying the nucleotide derivative complement in the image based on the label of the nucleotide derivative. In some embodiment, the sequencing-by-synthesis steps are repeated until substantially all of the first portion of the barcode has been decoded. In some embodiments, decoding the first portion of the barcode by sequencing-by-synthesis occurs prior to, contemporaneously with, or after removing the biological sample from the array.

IV. Terminology

Specific terminology is used throughout this disclosure to explain various aspects of the apparatus, systems, methods, and compositions that are described.

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can be spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(vi) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vii) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(viii) Primer Extension

A "primer extension" refers to any method where two nucleic acid sequences become linked (e.g., hybridized) by an overlap of complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(ix) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(x) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(xi) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oNTM DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xii) Label, Detectable Label, and Optical Label

The terms "detectable label" and "label" are used interchangeably herein to refer to a directly or indirectly detectable moiety that is associated with (e.g., conjugated to) a molecule to be detected, e.g., a probe for in situ assay, or analyte. The detectable label can be directly detectable by itself (e.g., radioisotope labels or optical labels such as fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature. For example, detectably labeled features can include a fluorescent, a colorimetric, or a chemiluminescent label attached to an analyte, probe, or bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore.

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and—methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLES

The following example is included for illustrative purposes only and is not intended to limit the scope of the present disclosure.

Example 1—Bi-Directional In Situ Sequencing

This Example describes an exemplary method of bi-directional sequencing. In some examples, the bi-directional sequencing comprises performing a sequencing-by-ligation reaction from the 5' end of the anchor, and performing a synthesis (extension) reaction from the 3' end of the anchor. The synthesis (extension) reaction can be a polymerase-chain-reaction, and isothermal amplification reaction, a rolling circle amplification, a sequencing-by-synthesis (SBS) reaction, or any suitable primer extension or synthesis reaction known in the art. Exemplary protocols for sequencing-by-ligation and synthesis reactions are described below. The sequencing-by-ligation and synthesis reactions can be performed in any order.

Sequencing-by-Ligation (SBL)

Sequencing-by-ligation is used to analyze a region of interest located 3' to an adaptor region of the nucleic acid that hybridizes to an anchor by ligating detection probes to the 5' end of the anchor.

In some examples, sequencing-by-ligation uses a combinatorial sequencing approach, wherein in a first set of detection probes comprise one or more known nucleotides at a first position of the sequencing probe, and a second round of detection probes comprise one or more known nucleotides at a second position of the sequencing probe. Each detection probe comprises an optical label corresponding to the known nucleotide or the known sequence of nucleotides.

Ligation of the detection probe to the anchor depends on complementarity of the known nucleotide(s) of the detection probe with the target nucleic acid at the corresponding position (e.g., a known nucleotide in the first position at the 3' end of the detection probe must correspond to the nucleotide immediately adjacent to the known adaptor sequence of the nucleic acid, a known nucleotide in the second position at the 3' end of the detection probe must correspond to the nucleotide in the second position adjacent to the known adaptor sequence of the nucleic acid, and so on). After ligation of the detection probe to the anchor, an image is obtained of the optical label associated with the first detection probe while the detection probe is hybridized to the first region of interest. The nucleotide(s) of the region of interest is/are determined by identifying the complement(s) of the known nucleotide(s) at the known sequence position of the first sequencing probe.

Optionally, a kinase can add a phosphate group to the cleaved first detection probe if the nuclease reaction removes the free 5' phosphate necessary for ligation of the additional sequencing probe. Prior to hybridization of the second round of detection probes, the first detection probe can be contacted with a nuclease where the nuclease removes cleaves the first detection probe from the anchor, and the first detection probe can be removed leaving the 5' phosphate of the anchor for ligation of the second sequencing probe. Alternatively, the ligated anchor-detection probe complex can be removed and the nucleic acid can be contacted with a new anchor for ligation to a detection probe of the second round of detection probes.

After ligation of the second detection probe to the anchor, an image is obtained of the optical label associated with the second detection probe while the second detection probe is hybridized to the first region of interest. The nucleotide(s) of the region of interest is/are determined by identifying the complement(s) of the known nucleotide(s) at the known sequence position of the second sequencing probe.

These steps can be repeated in order to determine the sequence of the region of interest.

In some examples, sequencing-by-ligation comprises ligation of a series of one or more detection probes to the 5' end of the anchor. In some examples, each detection probe in the composition of detection probes includes one or more (e.g., 1 or 2) known nucleotides at the 3' sequence position and a known, optical label, wherein the optical label is associated with the sequence of known nucleotide(s) at the known 3' sequence position. Therefore, each optical label is associated with an nucleotide or sequence of nucleotides (e.g., 2 nucleotides) at the terminal 3' position of a sequencing probe. For example, 4 optical labels can be used to correspond to detection probes comprising a single known nucleotide (4 possible nucleotides), or 16 optical labels can be used to correspond to detection probes comprising a sequence of two known nucleotides (16 possible known sequence combinations). A first detection probe from the composition detection probes is coupled to the free 5' end of the anchor by ligation. In a SBL reaction, a detection probe (e.g., the first sequencing probe) is hybridized to the first region of interest and ligated to the free 5' end of the anchor, wherein ligation of the probe depends on complementarity of the 3' sequence position of the detection probe to the first unpaired nucleotide of the region of interest. An image is obtained of the optical label associated with the first detection probe while the detection probe is hybridized to the first region of interest. One or more nucleotides of the region of interest is determined by identifying the complement of the one or more known nucleotides at the 3' sequence position of the first sequencing probe.

FIGS. 3A-3C show an exemplary variation of SBL, wherein each detection probe comprises a known set of dinucleotides, and a sequence of one or more degenerate (N) nucleotides and/or universal nucleotides (Z). As shown in FIG. 3B, in some embodiments, the detection probe comprises a cleavage site, and a cleavage agent can be used to cleave at least the detectable label from the end of the detection probe, thereby regenerating a 5' phosphate. As shown in FIG. 3C, hybridization and ligation of detection probes can be repeated to determine a sequence of the first region of interest. As indicated by the dashed arrows, a synthesis reaction can be performed from the 3' end of the anchor or the ligation product (i.e., before or after SBL).

SBL can be repeated until substantially all of the first region of interest has been decoded. Prior to each additional round of SBL, the sample can be washed to remove unbound detection probes. In each additional round of SBL, a new composition of detection probes can be provided and one of the detection probes from the new composition (e.g., referred to as an additional sequencing probe) is coupled to the free 5' end of the first detection probe that was added in the immediately preceding round of SBL. Prior to adding the additional sequencing probe, the first detection probe can be contacted with a nuclease where the nuclease removes at least the 5' portion of the first detection probe that includes the optical label. Optionally, a kinase adds a phosphate group to the cleaved first detection probe if the nuclease reaction removes the free 5' phosphate necessary for ligation of the additional sequencing probe. In the additional round of SBL, hybridizing the additional to the second portion of the region of interest and ligating it to the ligated anchor-probe complex includes contacting the nucleic acid with a composition of detection probes as described above. The additional detection probe hybridizes to the next unpaired nucleotide of the region of interest based on complementarity of the 3' nucleotide of the additional detection probe to the next unpaired nucleotide sequence of the first region of interest. An image is obtained of the optical label associated with the additional detection probe while the additional detection probe is hybridized to the first region of interest. One nucleotide of the first region of interest is determined by identifying the complement of the known nucleotide at the 3' sequence position of the additional sequencing probe. Additional cycles of SBL are repeated until substantially all of the first region of interest has been decoded.

Synthesis Reactions from the 3' End of the Anchor

The 3' end of the anchor can be used to prime a nucleic acid synthesis reaction or primer extension reaction. The synthesis reaction from the 3' end of the anchor can be used to analyze a second region of interest (e.g., located 5' to an adaptor region of the nucleic acid that hybridizes to an anchor) using the anchor as a primer. In some examples, the synthesis reaction can be a polymerase chain reaction (PCR), wherein the anchor is denatured from the nucleic acid, annealed, and extended in multiple cycles of amplification. In some examples, the synthesis reaction can comprise isothermal amplification. In some examples, the synthesis reaction can be a rolling circle amplification (e.g., of a circular probe or circularized padlock probe). FIGS. 5A-5B show an exemplary embodiment comprising contacting the sample with a contacting the sample with a primary probe comprising a sequence complementary to the second region of interest; and extending the anchor with a polymerase using the primary probe as a template. The primary probe can be a padlock probe. As shown in FIG. 5A, the padlock probe can be circularized using the second region of interest as a template. Alternatively, the padlock probe can be circularized using the anchor as a template, as shown in FIG. 5B. In some embodiments, extension step in (b)

comprises a rolling circle amplification (RCA) of a primary probe that is circular or circularized.

In some examples, the synthesis reaction is a sequencing-by-synthesis ("SBS") reaction. SBS analysis can generate a series of images, which can then be processed to read the sequence of the nucleic acids in a sample.

Example 2—Decoding Barcodes on an Array

This Example describes an exemplary method of bi-directional sequencing to decode a first portion and a second portion of a barcode flanking a known sequence. Optionally, the known sequence is a "constant" sequence among multiple target nucleic acids (e.g., multiple capture probes), and the same anchor can be used to decode the first and second portion of the barcode.

FIG. 1 shows an exemplary method for in situ sequencing of a first and second region of interest (e.g., a barcode comprising a first portion and a second portion flanking the adaptor region) using bi-directional sequencing. In a non-limiting example, a barcode is decoded using bi-directional sequencing, and the first and second regions of interest are first and second portions of a barcode. In some examples, the method includes providing an array including a capture probe, where the capture probe includes a barcode, an adaptor region (which can be a constant sequence common among capture probes), and a capture domain. The barcode includes a first portion and a second portion flanking the adaptor region. An anchor hybridizes to the adaptor region.

Figure 2A:
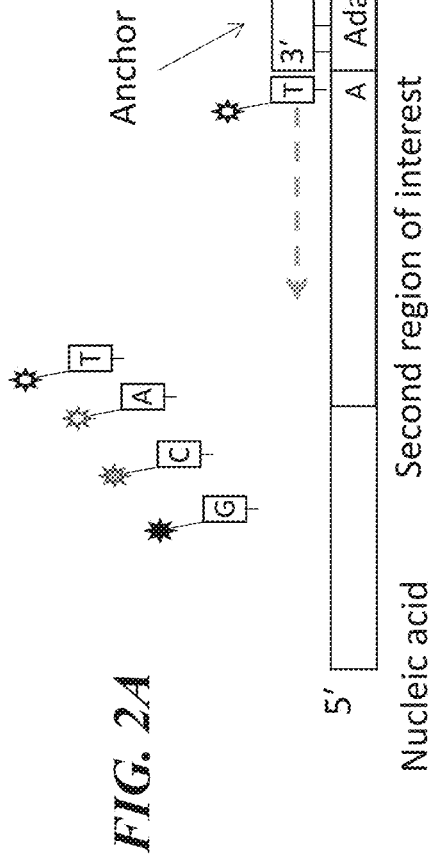
FIG. 2A shows an exemplary method comprising sequencing-by-synthesis (SBS) to extend the anchor in the 5' to 3' direction, thereby determining a sequence of the second region of interest. Although the figure depicts an SBS reaction extending an anchor prior to probe ligation to the anchor, any number (e.g., one or more) of cycles of nucleotide incorporation and signal detection for SBS can be performed simultaneously with, before, or after any number (e.g., one or more) of cycles of probe ligation and signal detection for SBL. One or more cycles of SBS and/or one or more cycles of SBL can be alternated and repeated in any suitable order.
Figure 2B:
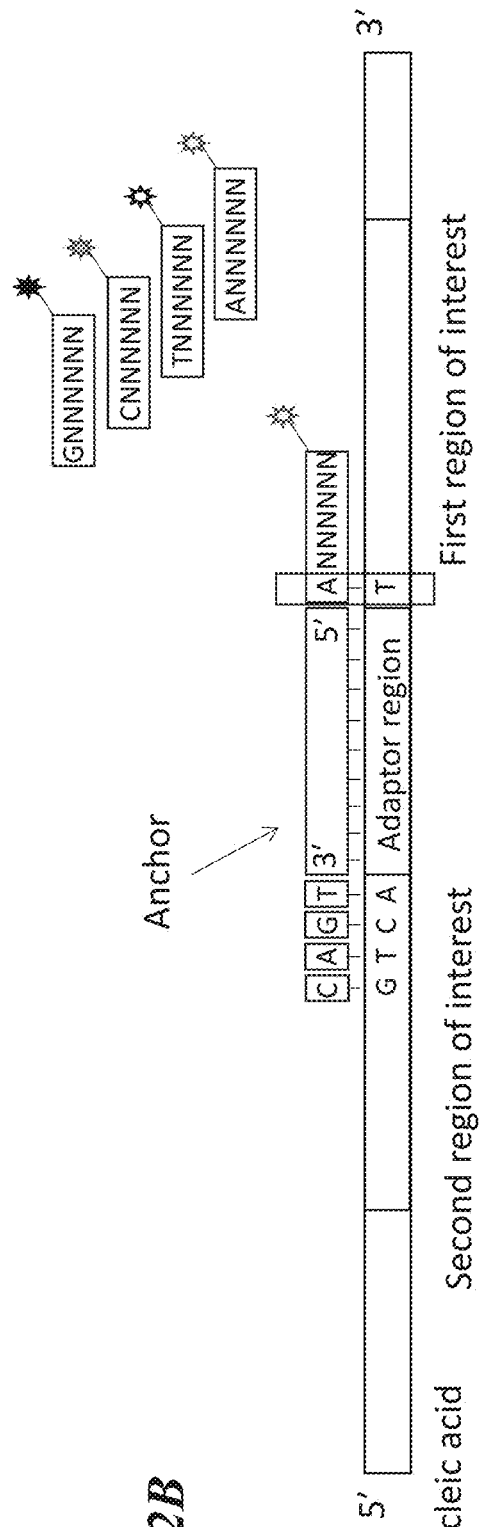
FIG. 2B shows an exemplary method comprising SBL following SBS, comprising ligating a detection probe (e.g., a sequencing probe) complementary to the first region of interest to the 5' end of the anchor; and detecting a signal associated with the detectable label of the detection probe ligated to the anchor to generate a ligation product. The contacting, ligating, and detecting steps can be repeated to determine a sequence of the first region of interest. Although
Figure 4:
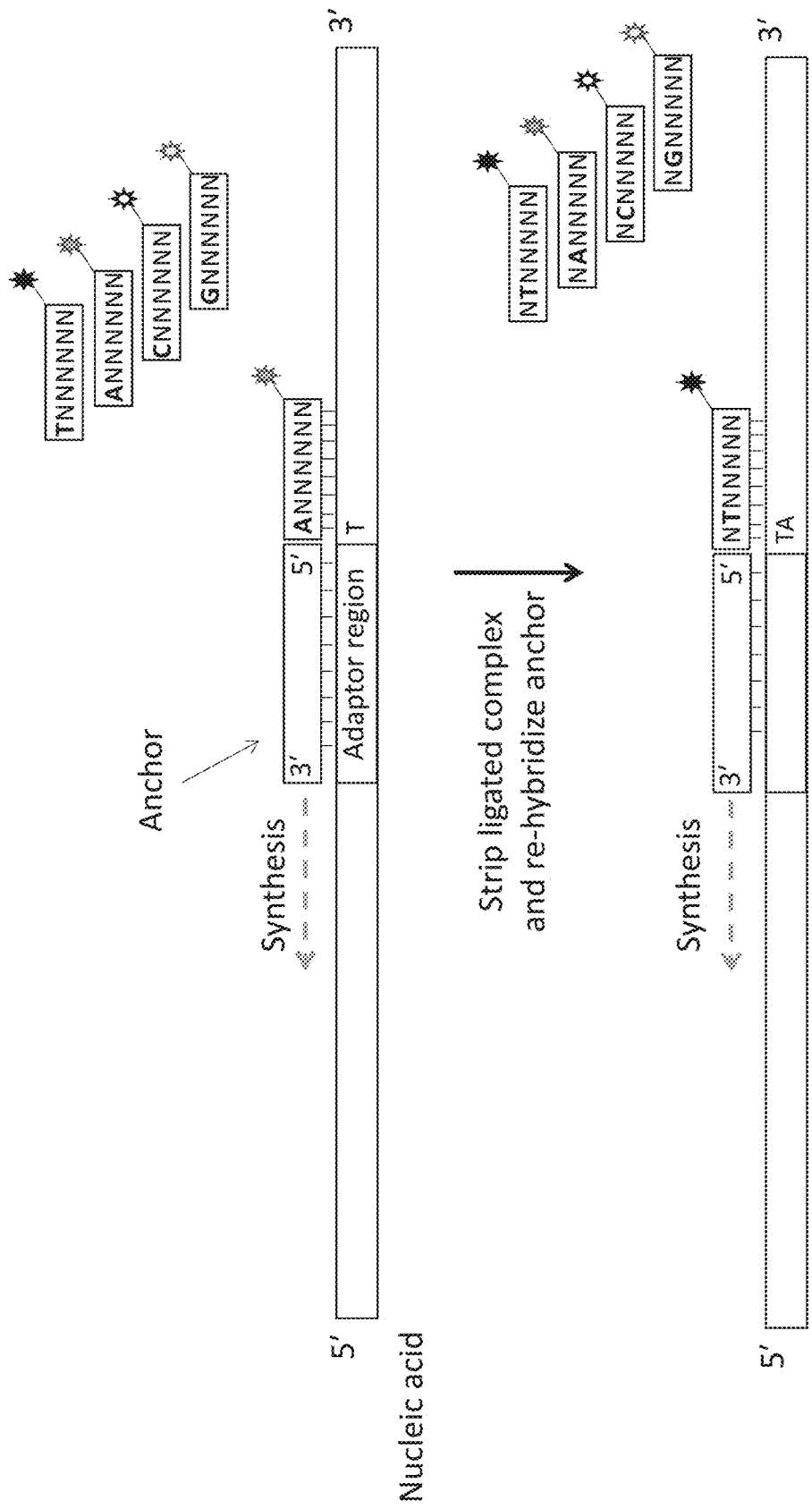
FIG. 4 shows an exemplary variation of SBL wherein the position of the interrogatory nucleotide or sequence (e.g., a single interrogatory nucleotide as shown in the figures) is shifted in each cycle of SBL, thereby determining a sequence of the first region of interest. After each cycle, the ligated complex can be stripped and the same anchor can be re-hybridized for an additional cycle of SBL. As indicated by the dashed arrow, the anchor or ligation product thereof can be extended in the 3' to 5' direction using a polymerase in a reaction using the second region of interest as a template. The anchor, extended anchor, ligation product comprising the anchor, or extended anchor ligation product can be stripped after one or more cycles of synthesis (e.g., anchor extension or SBS) and/or SBL. In some embodiments, the anchor, extended anchor, ligation product comprising the anchor, or extended anchor ligation product can be cleaved prior to stripping (e.g., cleaved into two or more separate molecules).

As seen in FIG. 2A, sequencing-by-synthesis ("SBS") is used to decode the second region of interest (e.g., a portion of a barcode flanking the adaptor region). To perform SBS, the capture probe, with the anchor hybridized to the adaptor region, is contacted with a plurality of nucleotide derivatives and a composition including a DNA polymerase (not depicted). A nucleotide derivative includes a nucleic acid having a 3' blocking group and optionally an optical label. The plurality of nucleotide derivatives include 5' triphosphates of 2'deoxyadenosine, 2'-deoxyguanosine, 2'-deoxycytidine and 2'-deoxythymidine, where each nucleotide derivative of the plurality of nucleotide derivative (e.g., 2'deoxyadenosine, 2'-deoxyguanosine, 2'-deoxycytidine and 2'-deoxythymidine) includes a 3' blocking group and optionally an optical label distinguishable from the optical labels of the other pluralities of nucleotide derivatives. In the first SBS reaction, the nucleotide derivative is coupled to the free 3' end of the anchor based on the complementarity of the nucleotide derivative to the first nucleotide of the first portion of the second region of interest. An image is obtained of the optical label associated with the nucleotide derivative while the nucleotide derivative is hybridized to the first position of the second region of interest. Based on the image, the first nucleotide in the second region of interest is determined by identifying the nucleotide derivative complement in the image based on the optical label of the nucleotide derivative.

SBS is repeated until substantially all of the second region of interest has been decoded. In each additional round of SBS, an additional nucleotide derivative is coupled to the free 3' end of the nucleotide derivative that was added in the immediately preceding round of SBS. Each additional nucleotide derivative includes one of a 5' triphosphates of 2'deoxyadenosine, 2'-deoxyguanosine, 2'-deoxycytidine and 2'-deoxythymidine, and where each nucleotide derivative of the plurality of nucleotide derivatives includes a 3' blocking group and optionally an optical label distinguishable from the optical labels of the other pluralities of nucleotide derivatives. Prior to coupling, the 3' blocking group of the hybridized nucleotide derivative is removed, and an OH group is added at the 3' position. The nucleotide derivative then hybridizes based on the complementarity of the nucleotide derivative to the next unpaired nucleotide of the second region of interest. An image is obtained of the optical label associated with the nucleotide derivative while the nucleotide derivative is hybridized to the second region of interest. Based on the image, the position of the hybridized nucleotide in the second region of interest is determined by identifying the nucleotide derivative complement in the image based on the optical label of the nucleotide derivative. Additional cycles of SBS are repeated until substantially all of the second region of interest has been decoded.

As seen in FIG. 2B, sequencing-by-ligation ("SBL") is used to decode the first region of interest (e.g., a portion of a barcode flanking the adaptor region). To perform SBL, the capture probe, with the anchor hybridized to the adaptor region, is contacted with a composition of detection probes. A detection probe includes an optical label and a nucleotide sequence. In a SBL reaction, ligating a detection probe that is hybridized to a first region of interest includes contacting the nucleic acid with a composition of detection probes. In some examples, each detection probe in the composition of detection probes includes a known nucleotide at the 3' sequence position and a known, optical label, wherein the optical label is associated with the plurality of nucleotide at the known 3' sequence position. Therefore, each optical label is associated with an identified plurality of nucleotide at the terminal 3' position of a sequencing probe. A first detection probe from the composition detection probes is coupled to the free 5' end of the anchor. In a SBL reaction, a detection probe ("sequencing probe", e.g., the first sequencing probe) is hybridized to the first region of interest ligated to the available 5' end of the anchor or the available end of a ligation product, wherein the hybridization and ligation is based on complementarity of the 3' sequence position of the detection probe to the first unpaired nucleotide of the first region of interest. An image is obtained of the optical label associated with the first detection probe while the detection probe is hybridized to the first region of interest. One nucleotide of the first region of interest is determined by identifying the complement of the known nucleotide at the 3' sequence position of the first sequencing probe.

SBL is repeated until substantially all of the first region of interest has been decoded. Prior to each additional round of SBL, the nucleic acid (e.g., a capture probe or any of the nucleic acids described in Section II) can be washed to remove unbound detection probes. In each additional round of SBL, a new composition of detection probes is provided and one of the detection probes from the new composition (e.g., referred to as an additional sequencing probe) is coupled to the free 5' end of the first detection probe that was added in the immediately preceding round of SBL. Prior to adding the additional sequencing probe, the first detection probe is contacted with a nuclease where the nuclease removes at least the 5' portion of the first detection probe that includes the optical label. Optionally, a kinase adds a phosphate group to the cleaved first detection probe if the nuclease reaction removes the free 5' phosphate necessary for ligation of the additional sequencing probe. In the additional round of SBL, ligating the additional detection probe to the free 5' end of the anchor or anchor ligation product includes contacting the first region of interest with a composition of detection probes. Each plurality of detection probe in the composition of detection probes includes a known different nucleotide at a 3' sequence position and a known, different optical label, wherein the optical label is associated with the plurality of nucleotide at the known 3' sequence position. An additional detection probe from the composition of detection probes is coupled to the free 5' end of the first sequencing probe. The additional detection probe hybridizes to the next unpaired nucleotide of the first region of interest based on complementarity of the 3' nucleotide of the additional detection probe to the next unpaired nucleotide sequence of the first region of interest. An image is obtained of the optical label associated with the additional detection probe while the additional detection probe is hybridized to the first region of interest. One nucleotide of the first region of interest is determined by identifying the complement of the known nucleotide at the 3' sequence position of the additional sequencing probe. Additional cycles of SBL are repeated until substantially all of the first region of interest has been decoded.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a sample, comprising:
    (a) contacting the sample with a plurality of detection probes, wherein:
    the sample comprises a nucleic acid comprising non-overlapping first and second regions of interest flanking an adaptor region that hybridizes to an anchor,
        each detection probe comprises an interrogatory region and a detectable label, and
        wherein the plurality of detection probes comprise detection probes labeled with different detectable labels, wherein the detectable label of each detection probe in the plurality of detection probes corresponds to a nucleotide or sequence in the interrogatory region of the respective detection probe;
    ligating a detection probe of the plurality of detection probes to the anchor to generate a ligation product, wherein the detection probe of the plurality of detection probes is complementary to the first region of interest; and
    detecting a signal associated with the detectable label of the ligation product; and
    (b) binding a polymerase to the other end of the anchor and incorporating a nucleotide and/or analog thereof into the anchor by the polymerase to generate an extended anchor (i) using the second region of interest as a template, or (ii) using a primary probe bound to the second region of interest as a template, wherein the primary probe comprises a region that hybridizes to the anchor.

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
actgtccgat agttagactg                                            20

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
actgtccgat agttagact                                             19

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct

<400> SEQUENCE: 3
actgtccgat agttagac                                              18

2. The method of claim 1, further comprising detecting a signal associated with the polymerase and/or the nucleotide or analog thereof incorporated into the other end of the anchor.

3. The method of claim 2, wherein the incorporation of nucleotide and/or analog thereof and signal detection are repeated to perform sequencing by synthesis, thereby sequencing all or a portion of the second region of interest or primary probe bound thereto.

4. The method of claim 1, wherein step (b) comprises contacting the sample with a pool of nucleotides and/or analogs thereof.

5. The method of claim 4, wherein the pool of nucleotides and/or analogs comprises a terminator nucleotide or analog thereof.

6. The method of claim 1, further comprising incorporating one or more nucleotides or analogs thereof into the extended anchor.

7. The method of claim 1, wherein the first region of interest, the adaptor region, and the second region of interest are in the same molecule.

8. The method of claim 1, wherein the first region of interest and the second region of interest are in a first and a second molecule, respectively.

9. The method of claim 1, wherein the contacting, ligating, and detecting steps in (a) are repeated to perform sequencing by ligation, thereby sequencing all or a portion of the first region of interest.

10. The method of claim 1, wherein the method comprises repeating the contacting, ligating, and detecting steps in (a) and repeating the binding in (b).

11. The method of claim 10, wherein the anchor remains hybridized to the nucleic acid during one or more cycles of the repeated steps in (a) and/or (b).

12. The method of claim 1, wherein the nucleic acid is endogenous in the sample, and the contacting, ligating, and/or detecting steps in (a) and/or the binding step in (b) are performed in situ.

13. The method of claim 1, wherein the nucleic acid in the sample is a product of an endogenous molecule in the sample.

14. The method of claim 1, wherein the sample comprises a support.

15. The method of claim 14, wherein the support comprises a bead.

16. A method of analyzing a sample, comprising:

(a) contacting the sample with a plurality of detection probes, wherein the sample comprises a nucleic acid comprising a first region of interest and a second region of interest flanking an adaptor region that hybridizes to an anchor, wherein each detection probe comprises an interrogatory region and a detectable label, wherein the plurality of detection probes comprise detection probes labeled with different detectable labels, wherein the detectable label of each detection probe in the plurality of detection probes corresponds to a nucleotide or sequence in the interrogatory region of the respective detection probe;

ligating a detection probe of the plurality of detection probes to the anchor to generate a ligation product, wherein the detection probe of the plurality of detection probes is complementary to the first region of interest; and detecting a signal from the detectable label of the ligation product; and (b) contacting the sample with a primary probe comprising a sequence complementary to the second region of interest, wherein the primary probe comprises a region that hybridizes to the anchor; and extending the anchor with a polymerase using the primary probe as a template.

* * * * *